(12) United States Patent
Kirsch et al.

(10) Patent No.: US 6,596,728 B1
(45) Date of Patent: Jul. 22, 2003

(54) SUBSTITUTED 1,3-DIARYL-2-PYRID-2-YL-3-(PYRID-2-YLAMINO)PROPANOL DERIVATIVES, PROCESS FOR THEIR PREPARATION, PHARMACEUTICALS COMPRISING THESE COMPOUNDS AND THEIR USE

(75) Inventors: Reinhard Kirsch, Braunschweig (DE); Alfons Enhsen, Büttelborn (DE); Heiner Glombik, Hofheim (DE); Werner Kramer, Mainz-Laubenheim (DE); Eugen Falk, Frankfurt (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/410,083

(22) Filed: Oct. 1, 1999

(30) Foreign Application Priority Data

Oct. 2, 1998 (DE) .......................... 198 45 406

(51) Int. Cl.$^7$ ...................... A61K 31/505; A61K 31/44; C07D 401/00
(52) U.S. Cl. .................. 514/269; 514/274; 514/336; 514/357; 514/340; 514/341; 514/342; 544/310; 544/316; 546/256; 546/264
(58) Field of Search ................ 514/357, 171, 514/212, 256, 314, 332, 340, 269, 274, 336, 341, 342; 540/333, 334, 596; 544/310, 316; 546/256, 264

(56) References Cited

U.S. PATENT DOCUMENTS

| | | | |
|---|---|---|---|
| 5,874,451 A | 2/1999 | Glombik et al. | 514/357 |
| 6,245,744 B1 * | 6/2001 | Frick et al. | 514/25 |
| 6,303,639 B1 * | 10/2001 | Frick et al. | 514/342 |

FOREIGN PATENT DOCUMENTS

EP 0 869 121 A1 10/1998

OTHER PUBLICATIONS

Bowie et al., *Science*, vol. 247, pp. 1306–1310, 1990.*
Houghten et al. *Vaccines 86*, Cold Spring Harbor Laboratory, pp. 21–25, 1986.*
English Abstract, Derwent No. 98–508454.
Huang, Y. and Hall, IH, "Hypolipidemic effects of α, β, and γ–alkylaminophenone analogs in rodents," *Eur. J. Med. Chem.*, vol. 31, 1996, pp. 281–290.

* cited by examiner

Primary Examiner—Christopher S. F. Low
Assistant Examiner—Abdel A. Mohamed
(74) Attorney, Agent, or Firm—Finnegan, Henderson, Farabow, Garrett & Dunner, LLP

(57) ABSTRACT

Substituted 1,3-diaryl-2-pyridin-2-yl-3-(pyridin-2-ylamino) propanol derivatives of the formula (I), and salts thereof,

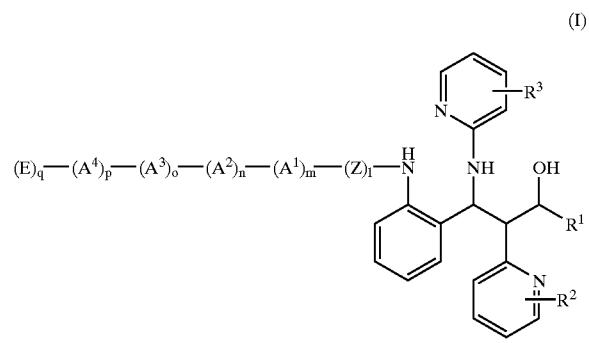

in which the radicals have the meanings given in the specification, and physiologically tolerated salts thereof and processes for their preparation are described. The compounds are suitable, for example, as hypolipidemic agents.

4 Claims, No Drawings

SUBSTITUTED 1,3-DIARYL-2-PYRID-2-YL-3-(PYRID-2-YLAMINO)PROPANOL DERIVATIVES, PROCESS FOR THEIR PREPARATION, PHARMACEUTICALS COMPRISING THESE COMPOUNDS AND THEIR USE

RELATED APPLICATIONS

Under the provisions of Section 119 of 35 U.S.C., Applicants hereby claim the benefit of the filing date of Federal Republic of Germany Patent Application Number 19845406.6, filed Oct. 2, 1998, which Application is hereby incorporated by reference.

The present invention relates to substituted 1,3-diaryl-2-pyridin-2-yl-3-(pyridin-2-ylamino)propanol derivatives and pharmaceutically tolerated salts and physiologically functional derivatives thereof.

BACKGROUND OF THE INVENTION

Several classes of active compounds for treatment of adiposity and disturbances in lipid metabolism have already been described, e.g.,
- polymeric adsorbers, such as cholestyramine,
- benzothiazepines (WO 93/16055),
- bile acid dimers and conjugates (EP 0 489 423), and
- 4-amino-2-ureido-pyrimidine-5-carboxamides (EP 0 557 879).

SUMMARY OF THE INVENTION

The object of the present invention is to provide further compounds displaying a therapeutically valuable hypolipidemic action.

(I)

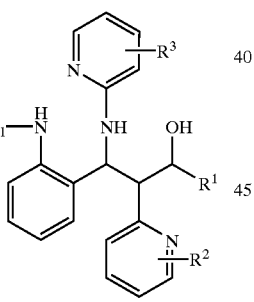

The present invention therefore relates to 1,3-diaryl-2-pyridin-2-yl-3-(pyridin-2-ylamino)propanol derivatives of formula (I) or salts thereof,
wherein:

Z is
—NH—($C_1$–$C_{16}$-alkyl)-(C=O)—,
—(C=O)—($C_1$–$C_{16}$-alkyl)-(C=O)—, or
—(C=O)-phenyl-(C=O)—;

$A^1$, $A^2$, $A^3$, $A^4$, each independently of one another is an amino acid radical, or an amino acid radical which is mono- or polysubstituted by amino acid-protective groups;

E is —$SO_2$—$R^4$ or —CO—$R^4$;

$R^1$ is phenyl, thiazolyl, oxazolyl, thienyl, thiophenyl, furanyl, pyridyl, or pyrimidyl, wherein the rings are unsubstituted, or substituted up to 3 times by F, Cl, Br, —OH, —$CF_3$, —$NO_2$, —CN, —$OCF_3$, —($C_1$–$C_6$)-alkyl, —O—($C_1$–$C_6$)-alkyl, —S—($C_1$–$C_6$)-alkyl, —SO—($C_1$–$C_6$)-alkyl, —$SO_2$—($C_1$–$C_6$)-alkyl, —($C_1$–$C_6$)-alkyl, —($C_3$–$C_6$)-cycloalkyl, —COOH, —COO—($C_1$–$C_6$)-alkyl, —COO—($C_3$–$C_6$)cycloalkyl, —$CONH_2$, —CONH—($C_1$–$C_6$)-alkyl, —CON[($C_1$–$C_6$)-alkyl]$_2$, —CONH—($C_3$–$C_6$)-cycloalkyl, —$NH_2$, —NH—CO—($C_1$–$C_6$)-alkyl, or —NH—CO-phenyl;

$R^2$ is H, —OH, —$CH_2OH$, or —OMe;

$R^3$ is H, F, methyl, or —OMe;

$R^4$ is —($C_1$–$C_{16}$-alkyl), —($C_0$–$C_{16}$-alkylene)-$R^5$, —(C=O)—($C_0$–$C_{16}$-alkylene)-$R^5$, —(C=O)—($C_0$–$C_{16}$-alkylene)-NH—$R^5$, —($C_1$–$C_8$-alkenylene)-$R^5$, —($C_1$–$C_8$-alkynyl), —($C_1$–$C_4$-alkylene)-S(O)$_r$—$R^5$, —($C_1$–$C_4$-alkylene)-O—$R^5$, or —($C_1$–$C_4$-alkylene)-NH—$R^5$;

$R^5$ is —COO—$R^6$, —(C=O)—$R^6$, —($C_1$–$C_6$-alkylene)-$R^7$, —($C_1$–$C_6$-alkenylene)-$R^7$, —($C_1$–$C_7$)-cycloalkyl, phenyl, naphthyl, thienyl, thiophenyl, furanyl, pyridyl, pyrimidyl, dihydropyrimidine-2,4-dion-6-yl, chromanyl, phthalimidoyl, or thiazolyl, wherein the rings are unsubstituted, or substituted up to 3 times by F, Cl, Br, —OH, —$CF_3$, —$NO_2$, —CN, —$OCF_3$, —($C_1$–$C_6$)-alkyl, —O—($C_1$–$C_6$)-alkyl, —S—($C_1$–$C_6$)-alkyl, —SO—($C_1$–$C_6$)-alkyl, —$SO_2$—($C_1$–$C_6$)-alkyl, —($C_1$–$C_6$)-alkyl, —($C_3$–$C_6$)-cycloalkyl, —COOH, —COO—($C_1$–$C_6$)-alkyl, —COO—($C_3$–$C_6$)-cycloalkyl, —$CONH_2$, —CONH—($C_1$–$C_6$)-alkyl, —CON[($C_1$–$C_6$)-alkyl]$_2$, —CONH—($C_3$–$C_6$)-cycloalkyl, —$NH_2$, —NH—CO—($C_1$–$C_6$)-alkyl, —NH—CO-phenyl, or pyridyl;

$R^6$ is H or —($C_1$–$C_6$)-alkyl;

$R^7$ is H, —($C_1$–$C_7$)-cycloalkyl, phenyl, naphthyl, thienyl, thiophenyl, furanyl, pyridyl, pyrimidyl, dihydropyrimidine-2,4-dion-6-yl, chromanyl, phthalimidoyl, or thiazolyl, wherein the rings are unsubstituted, or substituted up to 3 times by F, Cl, Br, —OH, —$CF_3$, —$NO_2$, —CN, —$OCF_3$, —($C_1C_6$)-alkyl, —O—($C_1$–$C_6$)-alkyl, —S—($C_1$–$C_6$)-alkyl, —SO—($C_1$–$C_6$)-alkyl, —$SO_2$—($C_1$–$C_6$)-alkyl, —($C_1$–$C_6$)-alkyl, —($C_3$–$C_6$)-cycloalkyl, —COOH, —COO—($C_1$–$C_6$)-alkyl, —COO—($C_3$–$C_6$)-cycloalkyl, —$CONH_2$, —CONH—($C_1$–$C_6$)-alkyl, —CON[($C_1$–$C_6$)-alkyl]$_2$, —CONH—($C_3$–$C_6$)-cycloalkyl, —$NH_2$, —NH—CO—($C_1$–$C_6$)-alkyl, or —NH—CO-phenyl;

l, q, m, n, o, p each independently of one another is 0 or 1, where the sum of l+q+m+n+o+p is greater than or equal to 1; and r is 0, 1, or 2;

with the proviso that in formula (I), when $R^1$ is unsubstituted phenyl, $R^2$ is H, $R^3$ is H, and l, m, n, o, and p are all zero, then $R^4$ is other than —$CH_3$ or —$C(CH_3)_3$.

Preferred compounds of formula (I) or salts thereof are those in which one or more radical(s) has or have the following meaning:

Z is
—NH—($C_1$–$C_{16}$-alkyl)-(C=O)—,
—(C=O)—($C_1$–$C_{16}$-alkyl)-(C=O)—, or
—(C=O)-phenyl-(C=O)—;

$A^1$, $A^2$, $A^3$, $A^4$, each independently of one another is an amino acid radical, or an amino acid radical which is mono- or polysubstituted by amino acid-protective groups;

E is —SO$_2$—R$^4$ or —CO—R$^4$;

R$^1$ is phenyl, thiazolyl, oxazolyl, thienyl, thiophenyl, furanyl, pyridyl, or pyrimidyl, wherein the rings are unsubstituted or substituted up to 3 times by F, Cl, Br, —OH, —CF$_3$, —NO$_2$, —CN, —OCF$_3$, —(C$_1$–C$_6$)-alkyl, —O—(C$_1$–C$_6$)-alkyl, —S—(C$_1$–C$_6$)-alkyl, —SO—(C$_1$–C$_6$)-alkyl, —SO$_2$—(C$_1$–C$_6$)-alkyl, —(C$_1$–C$_6$)-alkyl, —(C$_3$–C$_6$)-cycloalkyl, —COOH, —COO—(C$_1$–C$_6$)-alkyl, —COO—(C$_3$–C$_6$)-cycloalkyl, —CONH$_2$, —CONH—(C$_1$–C$_6$)-alkyl, —CON[(C$_1$–C$_6$)-alkyl]$_2$, —CONH—(C$_3$–C$_6$)-cycloalkyl, —NH$_2$, —NH—CO—(C$_1$–C$_6$)-alkyl, or —NH—CO-phenyl;

R$^2$ is H, —OH, —CH$_2$OH, or —OMe;

R$^3$ is H, F, methyl, or —OMe;

R$^4$ is —(C$_1$–C$_{16}$-alkyl), —(C$_0$–C$_{16}$-alkylene)-R$^5$, —(C=O)—(C$_0$–C$_{16}$-alkylene)-R$^5$, —(C=O)—(C$_0$–C$_{16}$alkylene)-NH—R$^5$, —(C$_1$–C$_8$-alkenylene)-R$^5$, —(C$_1$–C$_8$-alkynyl), —(C$_1$–C$_4$-alkylene)-S(O)$_r$R$^5$, —(C$_1$–C$_4$-alkylene)-O—R$^5$ or —(C$_1$–C$_4$-alkylene)-NH—R$^5$;

R$^5$ is —COO—R$^6$, —(C=O)—R$^6$, —(C$_1$–C$_6$-alkylene)-R$^7$, —(C$_1$–C$_6$-alkenylene)-R$^7$, —C$_1$–C$_7$)-cycloalkyl, phenyl, naphthyl, thienyl, thiophenyl, furanyl, pyridyl, pyrimidyl, dihydropyrimidine-2,4-dion-6-yl, chromanyl, phthalimidoyl, or thiazolyl, wherein the rings are unsubstituted or substituted up to 3 times by F, Cl, Br, —OH, —CF$_3$, —NO$_2$, —CN, —OCF$_3$, —(C$_1$–C$_6$)-alkyl, O—(C$_1$–C$_6$)-alkyl, —S—(C$_1$–C$_6$)-alkyl, —SO—(C$_1$–C$_6$)-alkyl, —SO$_2$—(C$_1$–C$_6$)-alkyl, (C$_1$–C$_6$)-alkyl, —(C$_3$–C$_6$)-cycloalkyl, —COOH, —COO—(C$_1$–C$_6$)-alkyl, —COO—(C$_3$–C$_6$)-cycloalkyl, —CONH$_2$, —CONH—(C$_1$–C$_6$)-alkyl, —CON[(C$_1$–C$_6$)alkyl]$_2$, —CONH—(C$_3$–C$_6$)-cycloalkyl, —NH$_2$, —NH—CO—(C$_1$–C$_6$)-alkyl, —NH—CO-phenyl, or pyridyl;

R$^6$ is H or —(C$_1$–C$_6$)-alkyl;

R$^7$ is H, —(C$_1$–C$_7$)-cycloalkyl, phenyl, naphthyl, thienyl, thiophenyl, furanyl, pyridyl, pyrimidyl, dihydropyrimidine-2,4-dion-6-yl, chromanyl, phthalimidoyl, or thiazolyl, wherein the rings are unsubstituted or substituted up to 3 times by F, Cl, Br, —OH, —CF$_3$, —NO$_2$, —CN, —OCF$_3$, —(C$_1$–C$_6$)-alkyl, —O—(C$_1$–C$_6$)-alkyl, —S—(C$_1$–C$_6$)-alkyl, —SO—(C$_1$–C$_6$)-alkyl, —SO$_2$—(C$_1$–C$_6$)-alkyl, —(C$_1$–C$_6$)-alkyl, —(C$_3$–C$_6$)-cycloalkyl, —COOH, —COO—(C$_1$–C$_6$)-alkyl, —COO—(C$_3$–C$_6$)-cycloalkyl, —CONH$_2$, —CONH—(C$_1$–C$_6$)-alkyl, —CON[(C$_1$–C$_6$)alkyl]$_2$, —CONH—(C$_3$–C$_6$)-cycloalkyl, —NH$_2$, —NH—CO—(C$_1$–C$_6$)-alkyl, or —NH—CO-phenyl;

l is 0 or 1;

m, n are 0;

o is 1;

p is 0 or 1;

q is 0 or 1; and r is 0, 1, or 2.

Particularly preferred compounds of formula (I) or salts thereof are those in which one or more radical(s) has or have the following meaning:

Z is
—NH—(C$_1$–C$_{12}$-alkyl)-(C=O)—,
—(C=O)—(C$_1$–C$_{12}$-alkyl)-(C=O)—, or
—(C=O)-phenyl-(C=O)—;

A$^1$, A$^2$, A$_3$, A$^4$ each independently of one another is an amino acid radical, or an amino acid radical which is mono- or polysubstituted by amino acid-protective groups;

E is —SO$_2$—R$^4$ or —CO—R$^4$;

R$^1$ is phenyl, thiazolyl, or oxazolyl, wherein the rings are unsubstituted or substituted up to 3 times by —(C$_1$–C$_6$)-alkyl;

R$^2$ is H, —OH, —CH$_2$OH, or —OMe;

R$^3$ is H, F, methyl, or —OMe;

R$^4$ is —(C$_1$–C$_{16}$-alkyl), —(C$_0$–C$_{16}$-alkylene)-R$^5$, —(C=O)—(C$_0$–C$_{16}$-alkylene)-R$^5$, —(C=O)—(C$_0$–C$_{16}$-alkylene)-NH—R$^5$, —(C$_1$–C$_8$-alkenylene)-R$^5$, —(C$_1$–C$_8$-alkynyl), —(C$_1$–C$_4$-alkylene)-S(O)$_r$—R$^5$, —(C$_1$–C$_4$-alkylene)-O—R$^5$, or —(C$_1$–C$_4$-alkylene)-NH—R$^5$;

R$^5$ is —COO—R$^6$, —(C=O)—R$^6$, —(C$_1$–C$_7$)-cycloalkyl, phenyl, naphthyl, thienyl, thiophenyl, furanyl, pyridyl, pyrimidyl, dihydropyrimidine-2,4-dion-6-yl, chromanyl, phthalimidoyl, or thiazolyl, wherein the rings are unsubstituted or substituted up to twice by F, Cl, Br, —OH, —CF$_3$, —NO$_2$, —CN, —OCF$_3$, —(C$_1$–C$_6$)-alkyl, —O—(C$_1$–C$_6$)-alkyl, —COOH, —COO—(C$_1$–C$_6$)-alkyl, —CONH$_2$, —CONH—(C$_1$–C$_6$)-alkyl, —CON[(C$_1$–C$_6$)alkyl]$_2$, —CONH—(C$_3$–C$_6$)-cycloalkyl, —NH$_2$, —NH—CO—(C$_1$–C$_6$)-alkyl, —NH—CO-phenyl, or pyridyl;

R$^6$ is H or —(C$_1$–C$_6$)-alkyl;

l, m, n is 0;

o is 1;

p is 0 or 1;

q is 0 or 1; and r is 0, 1, or 2.

DETAILED DESCRIPTION OF THE INVENTION

The term alkyl is understood as meaning straight-chain or branched hydrocarbon chains. The phrase "each independently of one another is" means each radical is individually selected without reference to the selection of the other radicals. Therefore, this phrase includes situations where the radicals are all identical to one another, where they are all different from one another, and where some radicals are identical to one another and others are different.

The terms amino acid(s) or amino acid radical(s) mean the stereoisomeric forms, i.e., D- or L-forms, of any of the following compounds:

| | | |
|---|---|---|
| alanine | glycine | proline |
| cysteine | histidine | glutamine |
| aspartic acid | isoleucine | arginine |
| glutamic acid | lysine | serine |
| phenylalanine | leucine | threonine |
| tryptophan | methionine | valine |
| tyrosine | asparagine | |
| 2-aminoadipic acid | | 2-aminoisobutyric acid |
| 3-aminoadipic acid | | 3-aminoisobutyric acid |
| beta-alanine | | 2-aminopimelic acid |
| 2-aminobutyric acid | | 2,4-diaminobutyric acid |
| 4-aminobutyric acid | | desmosine |
| piperidic acid | | 2,2-diaminopimelic acid |
| 6-aminocaproic acid | | 2,3-diaminopropionic acid |
| 2-aminoheptanoic acid | | N-ethylglycine |
| 2-(2-thienyl)-glycine | | 3-(2-thienyl)-alanine |
| penicillamine | | sarcosine |
| N-ethylasparagine | | N-methylisoleucine |
| hydroxylysine | | 6-N-methyllysine |
| allo-hydroxylysine | | N-methylvaline |
| 3-hydroxyproline | | norvaline |

| | |
|---|---|
| 4-hydroxyproline | norleucine |
| isodesmosine | ornithine |
| allo-isoleucine | 3-(2-naphthyl)alanine |
| azaglycine | N-cyclohexylglycine |
| 2,4-diaminobutyric acid | |

Abbreviation of the amino acids is in accordance with customary nomenclature (cf. Schröder, Lübke, The Peptides, Volume I, New York 1965, pages XXII–XXIII; Houben-Weyl, Methoden der Organischen Chemie (Methods of Organic Chemistry), Volume XV/1 and 2, Stuttgart 1974). The amino acid pGlu represents pyroglutamyl, Nal represents 3-(2-naphthyl)alanine, Azagly-$NH_2$ represents a compound of the formula $NH_2$—NH —$CONH_2$ and D-Asp represents the D-form of aspartic acid. Peptides are acid amides in their chemical nature and dissociate into amino acids on hydrolysis.

The present invention furthermore relates to processes for the preparation of compounds of formula (I) which comprise the following reaction equations (Equations 1 to 6).

The compounds of formula (I) and their salts according to the present invention are prepared starting from compounds of formulae VI or VII in stages from the free amino group or by coupling of segments by the general methods of peptide chemistry (Houben-Weyl *Methoden der Organischen Chemie*, Volume 15/1,2). The peptide couplings can be carried out, for example, with TOTU (for literature examples see: G. Breipohl, W. König EP 0460446; W. König, G. Breipohl, P. Pokomy, M. Birkner in E. Giralt and D. Andreu (Eds.) *Peptides* 1990, Escom, Leyden, 1991, 143–145) by the method of mixed anhydrides, via active esters, azides or by the carbodiimide method, in particular with the addition of substances which accelerate the reaction and prevent racemization, such as 1-hydroxybenzotriazole, N-hydroxysuccinimide, 3-hydroxy-4-oxo-3,4-dihydro-1,2,3-benzotriazine, or N-hydroxy-5-norbornene-2,3-dicarboximide, and furthermore using active derivatives of 1-hydroxybenzotriazole or anhydrides of phosphoric, phosphonic and phosphinic acids, at a reaction temperature of between −10° C. and the boiling point of the solvent, preferably between −5° C. and 40° C.

Suitable solvents for this are dimethylformamide, dimethylacetamide, N-methylpyrrolidone or dimethyl sulfoxide. If the solubility of the components allows, solvents such as methylene chloride, chloroform or tetrahydrofuran or mixtures of solvents can also be employed. Suitable methods are described in Meinhofer-Gross, *"The Peptides"* Academic Press, Volume I, (1979), among others.

If necessary to prevent side reactions, or for the synthesis of specific peptides, the functional groups in the amino acid side chain are additionally protected by suitable protective groups (see, for example, T. W. Greene, *"Protective Groups in Organic Synthesis"*). Primary examples are Arg(BOC)$_2$, Arg(Tos), Arg(Mts), Arg(Mtr), Arg(PMV), Asp(OBzl), Asp(OBut), Cys(4-MeBzl), Cys(Acm), Cys(SBut), Glu(OBzl), Glu(OBut), His(Tos), His(Fmoc), His(Dnp), His(Trt), Lys(Cl-Z), Lys(Boc), Met(O), Ser(Bzl), Ser(But), Thr(Bzl), Thr(But), Trp(Mts), Trp(CHO), Tyr(Br-Z), Tyr(Bzl) or Tyr(But).

The benzyloxycarbonyl (Z) radical, which can be split off by catalytic hydrogenation, the 2-(3,5-dimethyloxyphenyl)propyl(2)oxycarbonyl (Ddz) or trityl (Trt) radical, which can be split off by weak acids, and the 9-fluorenylmethyloxycarbonyl (Fmoc) radical, which can be split off by secondary amines, are typical examples of useful aminoprotective groups. The SH group of cysteine can be blocked by a number of protective groups. The trityl (Trt) radical and the S-tert-butyl (StBu) radical are generally used for this purpose. The trityl radical can be split off by iodine oxidation with formation of the cysteine compounds, or by reducing acid cleavage to give the cysteine compounds (*Liebigs Ann. Chem.* 1979, 227–247).

On the other hand, the S-tert-butyl radical is best split off reductively with tributylphosphine (*Aust. J. Chem.* 19 (1966) 2355–2360). OH and COOH functions in the side chains are best protected by the tert-butyl (tBu) radical, which can be split off under acid conditions (see also: Meienhofer-Gross: *"The Peptides"*, Volume 3). The compounds of formulae VI and VII are prepared as follows:

Equation 1

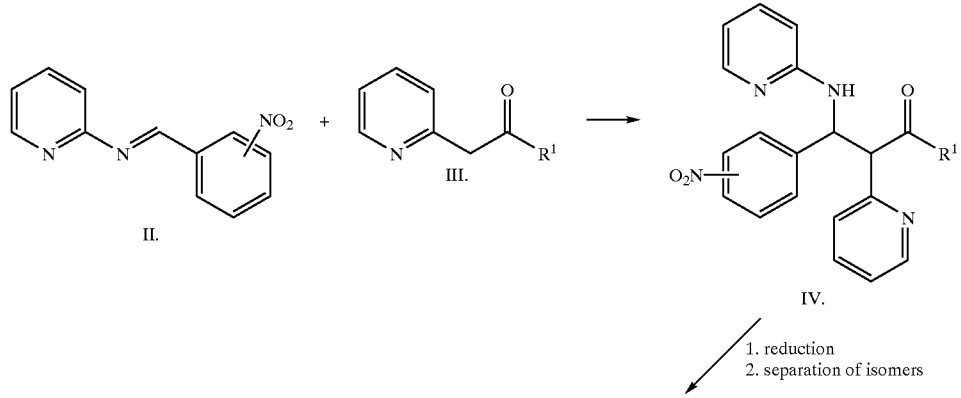

-continued

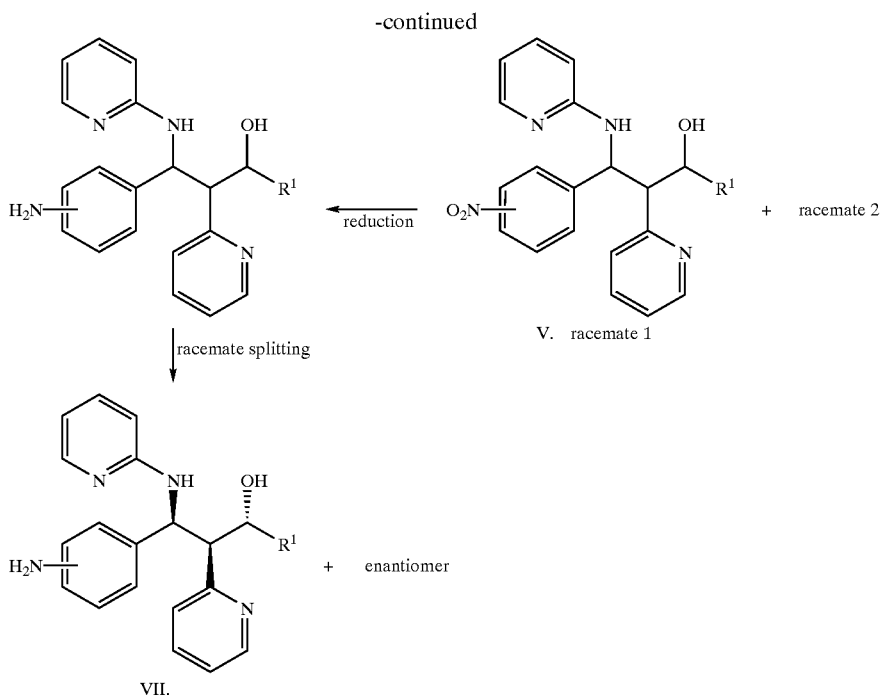

V. racemate 1

VII.

Compounds of type IV are obtained by reacting o-, m- or p-substituted imines of type II with a ketone III. The reaction can be carried out, for example, by mixing the two compounds in bulk, without a solvent, and subsequently heating the mixture, or in a suitable solvent such as ethanol, tetrahydrofuran (THF), toluene, diglyme or tetradecane, at temperatures of from 20° C. to 150° C.

The keto compounds of type IV are reduced with NaBH$_4$ or other suitable reducing agent in a suitable solvent, such as methanol, THF, or THF/water, at temperatures between −30° C. and +40° C. to give hydroxy compounds of type V. Two isomer mixtures (racemates) are usually obtained as the main products in the reduction. The different racemates can be separated from one another by fractional crystallization or by silica gel chromatography. The nitro group in compounds of type V can be reduced by known processes, such as, for example, catalytic hydrogenation with Pd or Pd-on-charcoal and H$_2$ in methanol.

The racemic compounds of type VI thus obtained can be separated further into their enantiomers. The racemate splitting of VI into enantiomers of type VII can be carried out by chromatography over chiral column material or by processes which are known from the literature, using optically active auxiliary reagents (cf. *J. Org. Chem.* 44, 1979, 4891).

In Preparation of compounds of formula (I) according to the present invention starting from compounds of type VI or VII is shown below.

Process A

Equation 2

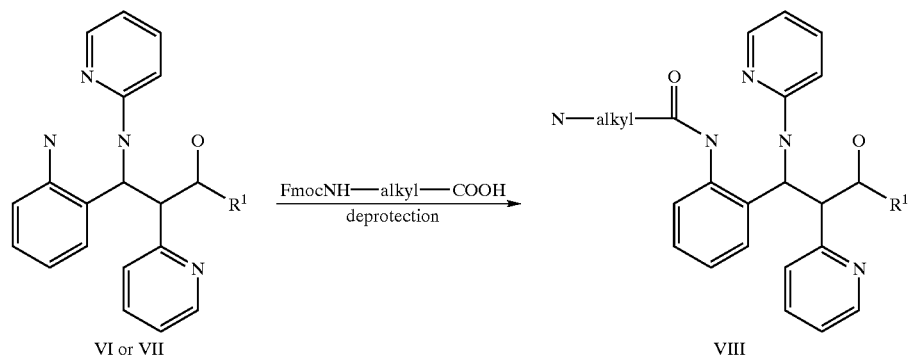

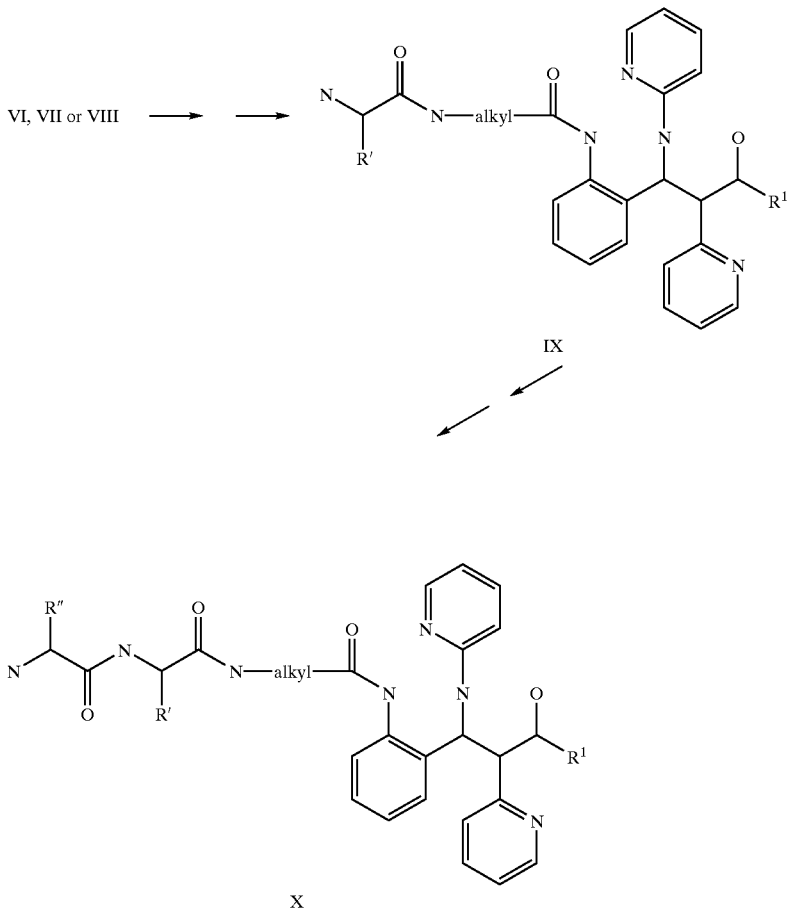

IX

X

Compounds of formula VI or VII are reacted with derivatives of aminoalkanecarboxylic acids. Peptide coupling processes are employed here. The aminoalkanecarboxylic acids, such as β-alanine or ω-aminoundecanoic acid, are protected with Fmoc groups, and corresponding nitro- or azidocarboxylic acids can also be used. After the protective group has been split off in a second step, or correspondingly after reduction of the azido or nitro group, compounds of formula VIII are obtained.

Compounds of formulae VI, VII or VIII can be reacted with amino-protected, for example Fmoc-protected, amino acids by peptide coupling processes, and the side chains can be protected with suitable orthogonal protective groups, or can be unprotected. After the coupling reaction, the protective group of the amino function is split off, in the case of Fmoc, for example, with piperidine in DMF. The compounds of type IX thereby obtained can be reacted in one to three further reaction sequences, i.e., amino acid coupling and splitting off of the amino-protective group, to give compounds of formula X.

The protective groups of the side chains of the amino acids $A^1$ to $A^4$, which number up to four, can be split off individually after each reaction sequence or together after all the coupling reactions, or all or some of them can also remain on the compounds X according to the present invention.

Process B

Equation 3

VI, VII, VIII or IX ⟶

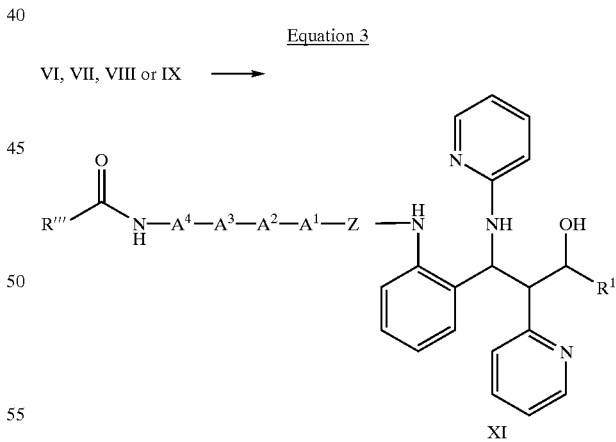

XI

The free amino functions of compounds of formulae VI, VII, VIII, IX or X are reacted with carboxylic acids, also by customary amide formation methods. Functional groups of the starting compounds susceptible to side reactions must be present in protected form, and can be split off after the reaction with the carboxylic acid, if necessary. The compounds according to the present invention of type XI are obtained therefrom.

Process C
Equation 4
VI, VII, VIII or IX ⟶
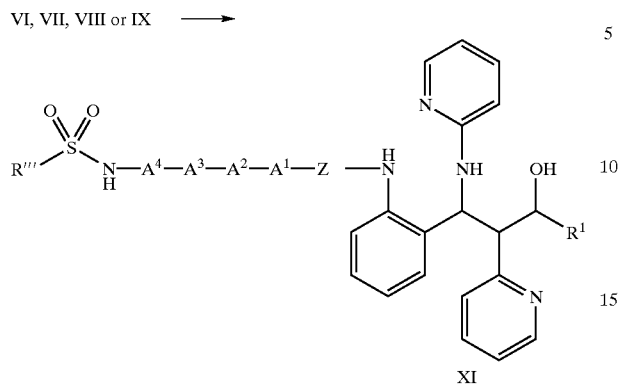
XI
Analogously to process B, the sulfonamide derivatives XII are obtained from the compounds of the formulae VI to IX. Accordingly, the amino functions of the starting compounds can be reacted, for example, with sulfonic acid chlorides in the presence of an auxiliary base in a suitable solvent.
Process D
Equation 5
VI or VII ⟶
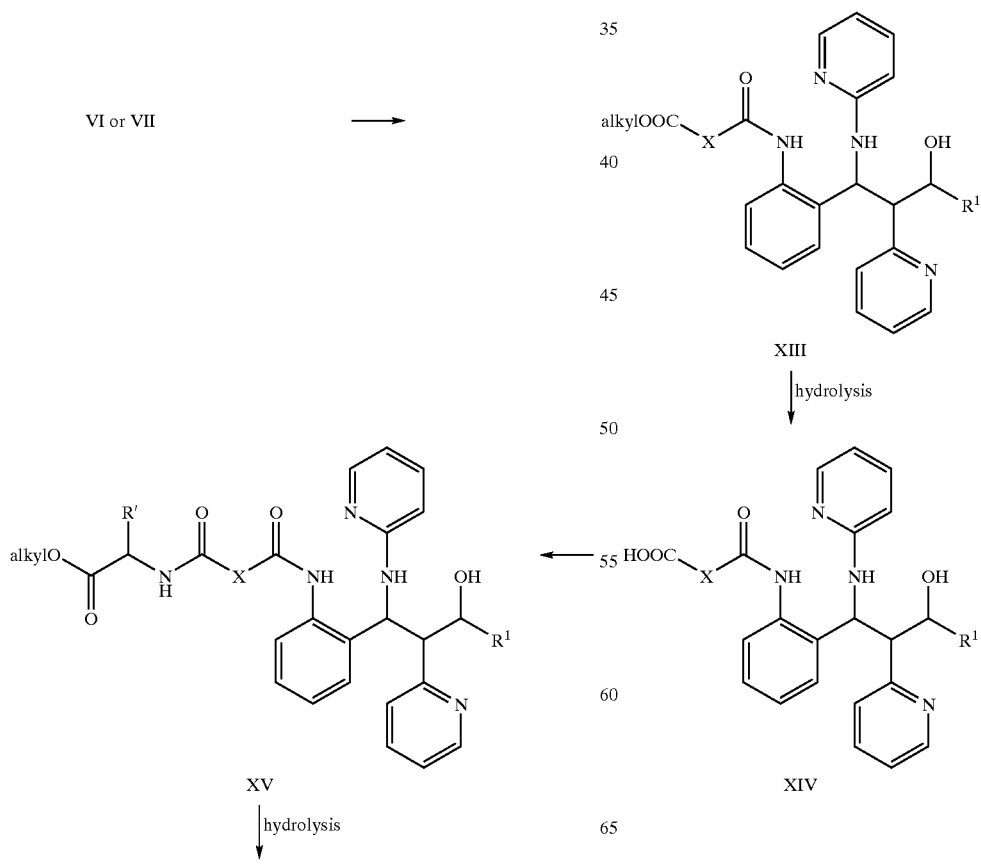

-continued

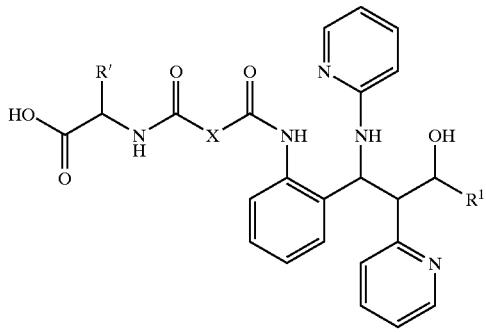

XVI

Compounds of type XIII can be obtained by reaction of dicarboxylic acid monoalkyl esters with compounds of type VI or VII, X representing an alkyl or a phenyl radical, in accordance with the claims. The reaction is carried out by customary peptide coupling processes. The alkyl ester function is then hydrolyzed to the carboxylic acid in order to obtain compounds of the formula XIV. The compounds XIV can also be obtained directly from the amines of type VI or VII by reaction with dicarboxylic acid anhydrides, for example, succinic anhydride, in the presence of a base. If the carboxylic acid function of the compounds XIV is reacted with amino acid alkyl esters which a protective group may carry in the side chain, compounds of formula XV are obtained. The compounds of formula XVI are in turn prepared therefrom by hydrolysis of the alkyl ester function.

Processes A–D can also be modified such that the compounds according to the reactions may be prepared by reactions on a solid phase. This is shown in process E as a general example.

Process E

Equation 6

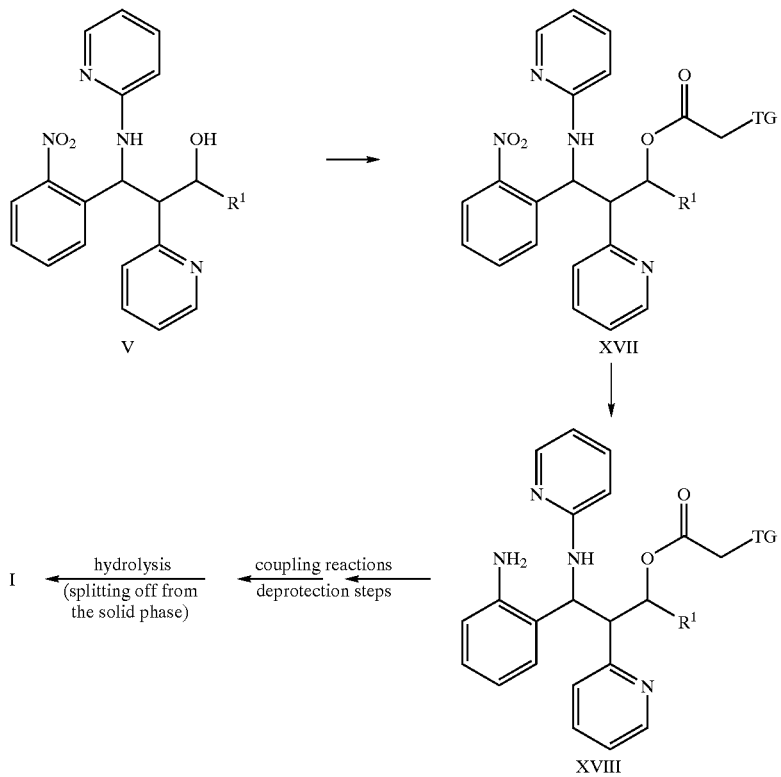

The compound of formula V is coupled to a modified polystyrene resin. For this, the carboxyl group of Carboxy-Tentagel (Rapp, Tübingen) is reacted with the OH function of the compound VI by esterification methods, for example, DCC or DMAP. The nitro group of compound XVII thus obtained is converted into the amino function by suitable methods, for example, $SuCl_2$ reduction processes. On derivative XVIII, which is bonded to the solid phase, the side chain $(E)_7$—$(A^4)_p$—$(A^3)_o$—$(A^2)_n$—$(A^1)_m$—$(Z)_e$ is built up to the desired length analogously to the peptide coupling processes already described. In the last step, the compounds of formula (I) according to the present invention are split off from the solid phase by hydrolysis of the ester group under basic conditions.

The radicals described as protective groups of amino acid side chains in the processes described can remain in the compounds according to the present invention or can be split off by known methods (see T. W. Greene, "*Protective Groups in Organic Synthesis*").

The compounds of formula (I) thus obtained can optionally be converted into their pharmaceutically tolerated salts or physiologically functional derivatives.

Because of their higher solubility in water compared with the starting or base compounds, pharmaceutically tolerated salts are particularly suitable for medical uses. These salts must have a pharmaceutically tolerated anion or cation. Suitable pharmaceutically tolerated acid addition salts of the compounds according to the present invention are salts of inorganic acids, such as hydrochloric, hydrobromic, phosphoric, metaphosphoric, nitric, sulfonic and sulfuric acid, and of organic acids, such as acetic, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acid. For medical purposes, the chlorine salt is particularly preferable. Suitable pharmaceutically tolerated basic salts are ammonium salts, alkali metal salts (such as sodium and potassium salts) and alkaline earth metal salts (such as magnesium and calcium salts).

Salts with an anion which is not pharmaceutically tolerated are also included in the scope of the present invention as beneficial intermediate products for the preparation or purification of pharmaceutically tolerated salts and/or for use in non-therapeutic applications, such as in vitro applications.

The term "physiologically functional derivative" used herein designates any physiologically tolerated derivative of a compound according to the present invention, i.e., an ester, which, when administered to a mammal, specifically a human, is capable of forming (either directly or indirectly) such a compound or an active metabolite thereof.

Prodrugs of the compounds according to the present invention are another aspect of the present invention. Such prodrugs can be metabolized in vivo to give a compound according to the invention. These prodrugs of the compounds of formula (I) are, for example esters, amides, aldehydes or alcohols obtainable from carboxy groups, or acyl derivatives like $(C_1-C_6)$-alkylcarbonyl, $(C_1-C_6)$-alkyloxycarbonyl, or aryl-$(C_1-C_4)$-alkyloxycarbonyl derivatives obtainable from acylatable groups including amino groups, imino groups, guanidino groups and amidino groups. These prodrugs can be active themselves or inactive.

The compounds according to the present invention can also exist in various polymorphous forms, for example, as amorphous and crystalline polymorphous forms. All the polymorphous forms of the compounds according to the present invention are included in the scope of the present invention and are a further aspect of the present invention.

All references to "compound(s) according to formula (I)" or "compound(s) of formula (I)" in the prestent invention relate to compound(s) of formula (I) as described above and their salts, solvates and physiologically functional derivatives as described herein.

The amount of a compound according to formula (I) necessary for achieving the desired biological effect depends on a number of factors, for example, the specific compound or salt chosen, the intended use, the mode of administration and the clinical condition of the patient.

In general, the daily dose is in the range from 0.3 mg to 100 mg, typically from 3 mg to 50 mg, per day per kilogram of bodyweight, for example 3–10 mg/kg/day. An intravenous dose can be, for example, in the range from 0.3 mg to 1.0 mg/kg, which can suitably be administered as an infusion of 10 ng to 100 ng per kilogram per minute. Suitable infusion solutions for this purpose can comprise, for example, from 0.1 ng to 10 mg, typically from 1 ng to 10 mg per milliliter. Individual doses can comprise, for example, from 1 mg to 10 g of the active compound. Thus, ampoules for injections can contain, for example, from 1 mg to 100 mg, and individual dose formulations for oral administration, such as, for example, tablets or capsules, can contain, for example, from 1.0 to 1000 mg, typically from 10 to 600 mg. In the case of pharmaceutically tolerated salts, the abovementioned weight data relate to the weight of the benzothiazepine ion derived from the salt. For prophylaxis or treatment of the abovementioned conditions, the compounds according to formula (I) can be used directly, but they are preferably present together with a tolerated excipient in the form of a pharmaceutical composition. The excipient must of course be tolerated in the sense that it is compatible with the other constituents of the composition and does not harm the health of the patient. The excipient can be a solid or a liquid or both and is preferably formulated with the compound as an individual dose, for example as a tablet, which can comprise from 0.05 to 95% by weight of the active compound. Further pharmaceutically active substances can also be present, including further compounds according to formula (I). The pharmaceutical compositions according to the present invention can be prepared by one of the known pharmaceutical methods, which substantially comprise mixing the constituents with pharmacologically tolerated excipients and/or auxiliaries.

Pharmaceutical compositions according to the present invention are those which are suitable for oral, rectal, topical, peroral (for example sublingual) and parenteral (for example subcutaneous, intramuscular, intradermal or intravenous) administration, although the most suitable mode of administration in each individual case depends on the nature and severity of the condition to be treated, and on the nature of the particular compound according to formula (I) used. Coated formulations and coated sustained-release formulations are also included in the scope of the present invention. Formulations which are resistant to acid and to gastric juice are preferred. Suitable coatings which are resistant to gastric juice include cellulose acetate phthalate, polyvinyl acetate phthalate, hydroxypropylmethyl-cellulose phthalate, and anionic polymers of methacrylic acid and methyl methacrylate.

Suitable pharmaceutical compounds for oral administration can be present in separate units, such as, for example, capsules, cachets, sucking tablets or tablets, each of which comprises a certain amount of the compound according to formula (I); as powders or granules; as a solution or suspension in an aqueous or non-aqueous liquid; or as an oil-in-water or water-in-oil emulsion. As already mentioned, these compositions can be prepared by any suitable pharmaceutical method which comprises a step in which the active compound and the excipient (which can consist of one or more additional constituents) are brought into contact. The compositions are in general prepared by uniform and homogeneous mixing of the active compound with a liquid and/or finely divided solid excipient, after which the product is shaped, if necessary. Thus, for example, a tablet can be prepared by pressing or shaping a powder or granules of the compound, optionally with one or more additional constituents. Pressed tablets can be prepared by tableting the compound in a free-flowing form, such as, for example, a powder or granules, optionally mixed with a binder, lubricant, inert diluent and/or one (or more) surface-active/dispersing agents, in a suitable machine. Shaped tablets can be prepared by shaping the pulverulent compound, which has been moistened with an inert liquid diluent, in a suitable machine.

Pharmaceutical compositions which are suitable for peroral (sublingual) administration include: sucking tablets, which comprise a compound according to formula (I) with a flavoring substance, usually sucrose, and gum arabic or tragacanth; and pastilles, which comprise the compound in an inert base, such as gelatin and glycerol, or sucrose and gum arabic.

Suitable pharmaceutical compositions for parenteral administration include sterile aqueous formulations of a compound according to formula (I), which are normally isotonic with the blood of the intended recipient. These formulations are generally administered intravenously, although the administration can also take place subcutaneously, intramuscularly or intradermally as an injection. These formulations are generally prepared by mixing the compound with water and rendering the resulting solution sterile and isotonic with blood. Injectable compositions according to the present invention in general comprise 0.1 to 5% by weight of the active compound.

Suitable pharmaceutical compositions for rectal administration are preferably in the form of individual-dose suppositories. These can be prepared by mixing a compound according to formula (I) with one or more conventional solid excipients, for example, cacao butter, and introducing the mixture formed into a mold.

Suitable pharmaceutical compositions for topical use on the skin are preferably in the form of an ointment, cream, lotion, paste, spray, aerosol or oil. Vaseline, lanolin, polyethylene glycols, alcohols and combinations of two or more of these substances can be used as excipients. The active compound is in general present in a concentration of 0.1 to 15% by weight of the composition, for example, 0.5 to 2%.

Transdermal administration is also possible. Suitable pharmaceutical compositions for transdermal applications can be in the form of individual patches which are suitable for long-term close contact with the epidermis of the patient. Such patches suitably comprise the active compound in an optionally buffered aqueous solution, dissolved and/or dispersed in an adhesion promoter or dispersed in a polymer. A suitable active compound concentration is about 1% to 35%, preferably about 3% to 15%. As a particular possibility, the active compound can be released by electroporation or iontophoresis, as described, for example, in *Pharmaceutical Research,* 2(6): 318 (1986).

The present invention furthermore relates both to isomer mixtures of formula (I) and to the pure enantiomers of formula (I).

The compounds of formula (I) and their pharmaceutically tolerated salts and physiologically functional derivatives thereof are ideal pharmaceuticals for treatment of disturbances in lipid metabolism, in particular, hyperlipidemia. The compounds of formula (I) are also suitable for influencing the serum cholesterol level and for prevention and treatment of arteriosclerotic symptoms. The following findings demonstrate the pharmacological activity of the compounds according to the present invention.

Biological testing of the compounds according to the present invention was carried out by determining the inhibition of [$^3$H]-taurocholate uptake in brush border membrane vesicles of the ileum of rabbits. The inhibition test was carried out as follows:

1. Preparation of Brush Border Membrane Vesicles from the Ileum of Rabbits

Brush border membrane vesicles from the intestinal cells of the small intestine were prepared by the so-called $Mg^{2+}$ precipitation method. Male New Zealand rabbits (2 to 2.5 kg body weight) were sacrificed by intravenous injection of 0.5 ml T61®, an aqueous solution of 2.5 mg tetracaine HCl, 100 m embutramide and 25 mg mebezonium iodide. The small intestine was removed and rinsed with ice-cold physiological saline solution. The terminal 7/10 of the small intestine (measured in the oral-rectal direction, i.e., the terminal ileum, which contains the active $Na^+$-dependent bile acid transportation system) was used for preparation of the brush border membrane vesicles. The intestines were frozen in plastic bags under nitrogen at –80° C. For preparation of the membrane vesicles, the frozen intestines were thawed at 30° C. in a water bath. The mucosa was scraped off and suspended in 60 ml of ice-cold 12 mM TRIS/HCl buffer (pH 7.1)/300 mM mannitol, 5 mM EGTA/10 mg/l of phenylmethylsulfonyl fluoride/1 mg/l of trypsin inhibitor from soybeans (32 U/mg)/0.5 mg/l of trypsin inhibitor from bovine lung (193 U/mg)/5 mg/l of bacitracin. After dilution to 300 ml with ice-cold distilled water, the mixture was homogenized with an Ultraturrax (18-rod, IKA Werk Staufen, Germany) for 3 minutes at 75% of the maximum output by cooling with ice. After addition of 3 ml of 1 M $MgCl_2$ solution (final concentration 10 mM), the mixture was allowed to stand for exactly 1 minute at 0° C. The cell membranes aggregate by addition of $Mg^{2+}$ and precipitate, with the exception of the brush border membranes. After centrifugation at 3000×g (5000 rpm, SS-34 rotor) for 15 minutes, the precipitate was discarded land the supernatant, which contains the brush border membranes, was centrifuged at 48000×g (20000 rpm, SS-34 rotor) for 30 minutes. The supernatant was discarded, and the precipitate was rehomogenized in 60 ml of 12 mM TRIS/HCl buffer (pH 7.1)/60 mM mannitol, 5 mM EGTA with a Potter Elvejhem homogenizer (Braun, Melsungen, 900 rpm, 10 strokes). After addition of 0.1 ml of 1 M $MgCl_2$ solution and incubation for 15 minutes at 0° C., centrifugation was again carried out at 3000×g for 15 minutes. The supernatant was then centrifuged again at 48000×x g (20000 rpm, SS-34 rotor) for 30 minutes. The precipitate was taken up in 30 ml of 10 mM TRIS/HEPES buffer (pH 7.4)/300 mM mannitol and resuspended homogeneously by 20 strokes in a Potter Elvejhem homogenizer at 1000 rpm. After centrifugation at 48000×g (20000 rpm, SS-34 rotor) for 30 minutes, the precipitate was taken up in 0.5 to 2 ml of TRIS/HEPES buffer (pH 7.4)/280 mM mannitol (final concentration 20 mg/ml) and resuspended with the aid of a Tuberculin syringe with a 27-gauge needle. The vesicles were either used for transportation investigations directly after preparation or stored at –196° C. in 4 mg portions in liquid nitrogen.

2. Inhibition of the $Na^+$-dependent [$^3$H]taurocholate Uptake in Brush Border Membrane Vesicles of the Ileum The uptake of substrates in the brush border membrane vesicles described above was determined by means of the so-called membrane filtration technique. 10 µl of the vesicle suspension (100 µg of protein) were pipetted as drops onto the wall of a polystyrene incubation tube (11×70 mm) which contained the incubation medium with the corresponding ligands (90 µl). The incubation medium comprised 0.75 µl=0.75 µCi [$^3$H(G)]-taurocholate (specific activity: 2.1 Ci/mmol)/0.5 µl of 10 mM taurocholate/8.75 µl of sodium transportation buffer (10 mM TRIS/HEPES (pH 7.4)/100 mM mannitol/100 mM NaCl) (Na-T-P) or 8.75 µl of potassium transportation buffer (10 mM TRIS/HEPES (pH 7.4)/100 mM mannitol/100 mM KCl) (K-T-P) and 80 µl of the inhibitor solution in question, dissolved in Na-T buffer or K-T-buffer, depending on the experiment. The incubation medium was filtered through a polyvinylidenefluoride membrane filter (SYHV LO 4NS, 0.45 µm, 4 mm Ø, Millipore, Eschborn, Germany). Mixing the vesicles with the incubation medium started the transportation measurement. The concentration of taurocholate in the incubation batch was 50 µM. After the desired incubation time (usually 1 minute), the transportation was stopped by addition of 1 ml of ice-cold stopping solution (10 mM TRIS/HEPES (pH 7.4)/150 mM KCl). The mixture formed was immediately filtered with suction under a vacuum of between 25 and 35 mbar over a membrane filter of cellulose nitrate (ME 25, 0.45 µm, 25 mm diameter, Schleicher & Schuell, Dassell, Germany). The filter was rinsed with 5 ml of ice-cold stopping solution.

To measure the uptake of the radioactively labeled taurocholate, the membrane filter was dissolved with 4 ml of the scintillator Quickszint 361 (Zinsser Analytik GmbH, Frankfurt, Germany) and the radioactivity was measured by liquid scintillation measurement in a TriCarb 2500 measuring apparatus (Canberra Packard GmbH, Frankfurt, Germany). The values measured were obtained as dpm (decompositions per minute) after calibration of the apparatus with the aid of standard samples and after correction for any chemiluminescence present.

The control values were each determined in Na-T-P and K-T-P. The difference between the uptake in Na-T-P and K-T-P gave the $Na^+$-dependent transportation content. The concentration of inhibitor at which the $Na^+$-dependent transporation content was inhibited by 50% as compared to the control is designated the $IC_{50}$ $Na^+$.

The pharmacological data comprise a test series in which the interaction of the compounds according to the present invention with the intestinal bile acid transportation system in the terminal small intestine was investigated. The results are summarized in Table 1.

Table 1 shows measurement values of the inhibition of the [$^3$H]-taurocholate uptake in brush border membrane vesicles of the ileum of rabbits. The quotients of the $IC_{50Na}$ values of the reference substance as taurochenodeoxycholate (TCDC) and of the particular test substance are stated.

TABLE 1

| Compounds from Example 1 | $\frac{IC_{50Na}\text{-TCDC (µmol)}}{IC_{50Na}\text{-compound (µmol)}}$ |
|---|---|
| 2c | 1.06 |
| 3 | 0.88 |
| 6 | 0.77 |
| 7 | 0.87 |
| 14 | 0.21 |
| 15 | 0.94 |
| 16 | 0.16 |
| 17 | 1.26 |
| 18 | 0.69 |
| 19 | 1.05 |
| 20 | 0.30 |
| 21 | 0.17 |
| 22 | 0.82 |
| 31 | 1.13 |
| 33 | 0.52 |
| 34 | 0.81 |
| 35 | 0.36 |
| 36 | 0.36 |
| 38 | 0.38 |
| 41 | 0.61 |
| 44 | 1.05 |

TABLE 1-continued

| Compounds from Example 1 | $\frac{IC_{50Na}\text{-TCDC (µmol)}}{IC_{50Na}\text{-compound (µmol)}}$ |
|---|---|
| 45 | 1.03 |
| 47 | 1.00 |
| 49 | 0.86 |
| 50 | 0.67 |
| 52 | 1.11 |
| 53 | 0.46 |
| 56 | 1.15 |
| 57 | 0.79 |
| 60 | 0.62 |
| 61 | 0.66 |
| 62 | 0.99 |
| 64 | 0.39 |
| 65 | 0.84 |
| 66 | 0.93 |
| 69 | 1.00 |
| 73 | 0.92 |
| 74 | 0.70 |
| 77 | 0.22 |
| 78 | 0.27 |
| 82 | 0.79 |
| 83 | 0.24 |
| 87 | 0.84 |
| 89 | 0.90 |
| 91 | 0.92 |
| 93 | 1.10 |
| 94 | 0.40 |
| 143 | 0.26 |
| 144 | 1.16 |
| 145 | 1.19 |
| 146 | 0.87 |
| 148 | 0.36 |
| 149 | 0.34 |
| 132 | 0.82 |
| 117 | 0.78 |
| 120 | 0.76 |

The following examples serve to illustrate the present invention in more detail, without limitation to the products and embodiments described in the examples.

EXAMPLE 1a

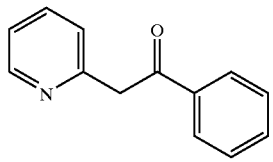

366 ml of 15% strength n-butyllithium in n-hexane were added dropwise to 50 g (0.54 mol) of picoline in 770 ml of tetrahydrofuran at −55° C. The mixture was warmed to room temperature and cooled again to −55° C. 77 g of N,N-dimethylbenzamide (0.52 mol) in 570 ml of tetrahydrofuran were slowly added dropwise, and the mixture was then warmed to room temperature and stirred for a further hour. After addition of 550 ml of 1N hydrochloric acid, the mixture was extracted three times with ethyl acetate and the organic phases were dried with $MgSO_4$ and evaporated. Distillation of the residue gave 47.5 g (47%) of the product. Boiling point 134–136° C./0.28 mbar.

EXAMPLE 1b

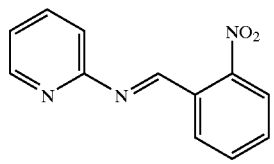

20.0 g (0.13 mol) of o-nitrobenzaldehyde, 12.5 g (0.13 mol) of 2-aminopyridine and 0.3 g of p-toluenesulfonic acid were heated under reflux in 150 ml of toluene for 2.5 hours, using a water separator. The solution was cooled and the precipitate formed was filtered off with suction and dried.

Yield: 18.1 g (60%) of product
Melting point: 93–95° C.
$C_{12}H_9N_3O_2$ (227) MS (FAB) 228 M+H+

EXAMPLE 1c

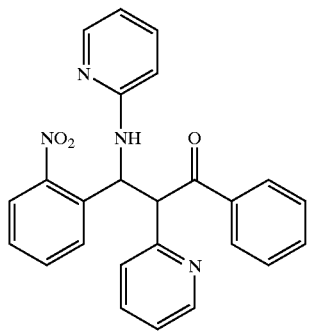

12.0 g (61 mmol) of the ketone from Example 1a and 15.0 g (66 mmol) of the imine from Example 1b were heated on a steam bath for 45 minutes. The reaction mixture was dissolved in ethanol, with heating. After cooling, the precipitate was filtered off with suction and recrystallized from ethanol.

Yield: 11.8 g (46%) of product
$C_{25}H_{20}N_4O_3$ (424.2) MS (FAB) 425 M+H+

EXAMPLE 1d

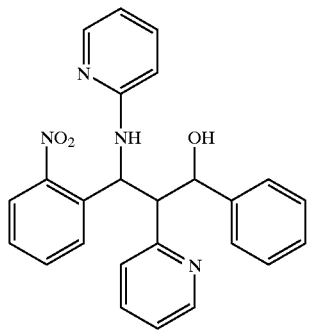

8.0 g (18.8 mmol) of the keto compound from Example 1c were dissolved in 300 ml of tetrahydrofuran/water 10:1, 4.67 g of sodium borohydride were added and the mixture was stirred at room temperature for 2 hours. The solution was then evaporated, 100 ml of 2N hydrochloric acid were added to the residue and the mixture was heated on a steam bath until everything had dissolved. After cooling, the mixture was rendered basic with 4N NaOH solution and extracted twice with ethyl acetate. The organic phases were dried with $MgSO_4$ and evaporated. The residue was chromatographed over silica gel (heptane/ethyl acetate 1:1). Two racemic compounds were obtained as the product.

1st fraction: 3.9 g (48%) of non-polar racemate (Example 1d/1)
$C_{25}H_{22}N_4O_3$ (426.2) MS (FAB) 427 M+H+

2nd fraction: 2.5 g (31%) of polar racemate (Example 1d/2)
$C_{25}H_{22}N_4O_3$ (426.2) MS (FAB) 427 M+H+

EXAMPLE 1e

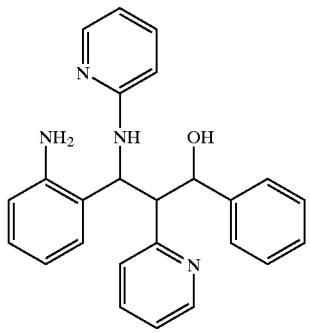

2.5 g (5.86 mmol) of the non-polar racemate from Example 1d/1 were dissolved in 300 ml of methanol, about 20 mg of Pd/C 10% were added and hydrogenation was carried out at room temperature under an $H_2$ atmosphere. The catalyst was filtered off and the solution was evaporated. The residue was chromatographed over silica gel (n-heptane/ethyl acetate 7:13).

Yield: 1.9 g (82%) of product
$C_{25}H_{24}N_4O$ (396.22) MS (FAB) 397 M+H+

EXAMPLE 1f

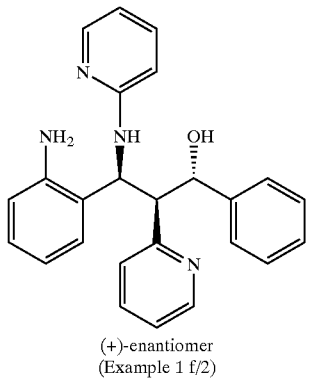

(+)-enantiomer
(Example 1 f/2)

100 mg of the racemic compound from Example 1e was separated into the enantiomers by preparative HPLC. The separation was carried out over a CSP-Chiralpak column (Daicel,Düsseldorf) with n-hexane/ethanol 4:1. 40 mg of the (−)-enantiomer (Example 1f/1) were obtained as the 1st fraction and 40 mg of the (+)-enantiomer (Example 1f/2) were obtained as the 2nd fraction.

EXAMPLE 1g

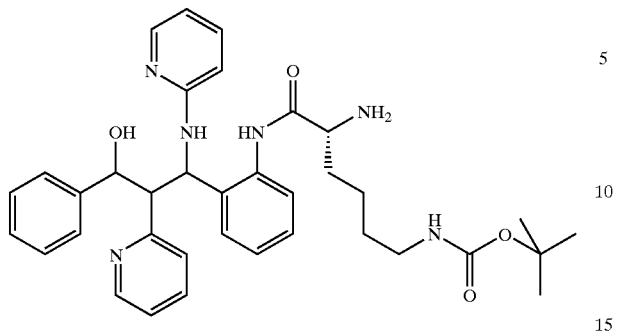

4.0 g (10.1 mmol) of the amino compound from Example 1e (non-polar racemate), 4.85 g (10.3 mmol) of N-Fmoc-D-Lys(BOC)OH, 4.0 g (12.2 mmol) of TOTU and 2.7 ml of triethylamine were dissolved in 300 ml of dimethylformamide and the mixture was stirred at room temperature for 2 hours. The reaction mixture was poured onto water and extracted twice with ethyl acetate. The organic phases were dried (MgSO$_4$) and evaporated. The residue was dissolved in 150 ml of dimethylformamide/piperidine 2:1, for splitting off the Fmoc group, and the solution was stirred at room temperature for 1 hour. It was poured onto water and extracted three times with ethyl acetate. The organic phases were dried (MgSO$_4$) and evaporated. Chromatography over silica gel (methylene chloride/methanol 9:1,) gave 4.0 g (63.5%) of the product.

$C_{36}H_{44}N_6O_4$ (624.3) MS (FAB) 625 M+H$^+$

EXAMPLE 1h

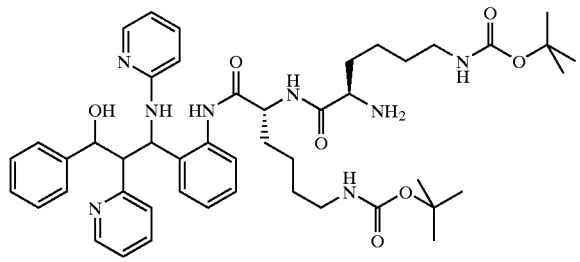

4.74 g (43%) of the product were obtained from 8.0 g of the compound from Example 1g (12.8 mmol) and 6.4 g (13.7 mmol) of N-Fmoc-D-Lys(BOC)OH by the process described under Example 1g.

$C_{47}H_{64}N_8O_7$ (852.5) MS (FAB) 853.5 M+H$^+$

EXAMPLE 2a

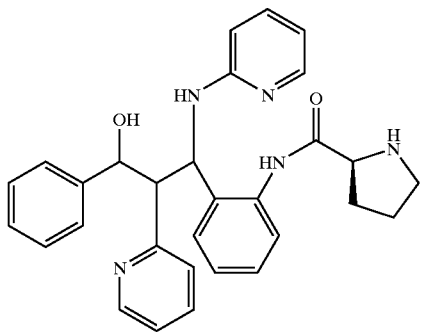

2.5 g (6.31 mmol) of the amino compound from Example 1e (non-polar racemate), 2.2 g (6.52 mmol) of Fmoc-L-proline, 2.5 g (7.62 mmol) of TOTU and 1.7 ml of triethylamine were dissolved in 100 ml of dimethylformamide and the solution was stirred at room temperature for 3 hours. The reaction mixture was evaporated to half of its original volume, water was added and the mixture was extracted three times with ethyl acetate. The organic phases were dried over MgSO$_4$ and evaporated. After chromatography over silica gel (ethyl acetate/n-heptane, 7:3), 3.85 g (85%) of product were obtained.

This Fmoc-protected intermediate product (3.6 g) was dissolved in 110 ml of piperidine/DMF, 1:10 and the solution was stirred at room temperature for 1 hour. The mixture was evaporated and chromatographed over silica gel (methylene chloride/methanol 19:1, then 9:1).

Yield: 1.8 g (72.5%)

$C_{30}H_{31}N_5O_2$ (493.2) MS (FAB) 494 M+H$^+$

EXAMPLE 2b

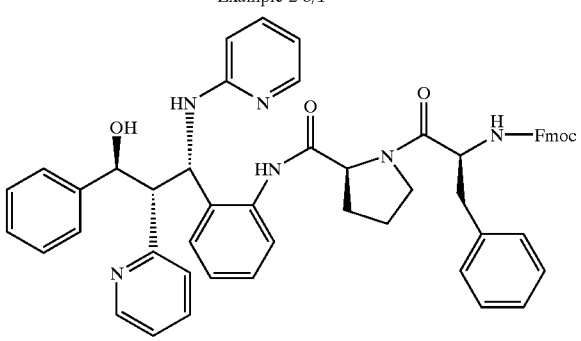

Example 2 b/1

Example 2 b/2

1.7 g (3.44 mmol) of the compound from Example 2a were stirred with 1.4 g (3.61 mmol) of Fmoc-L- phenylalanine, 1.9 g (5.80 mmol) of TOTU and 1.0 ml of triethylamine in 150 ml of DMF at room temperature for 4 hours. The reaction mixture was evaporated and the residue was chromatographed over silica gel (ethyl acetate/n-heptane 4:1). Two fractions were obtained:

1st fraction 1.28 g (43%) of non-polar diastereomer (Example 2b/1)

$C_{54}H_{50}N_6O_5$ (862.4) MS (FAB) 863.4 M+H$^+$

2nd fraction 0.82 g (28%) of polar diastereomer (Example 2b/1)

$C_{54}H_{50}N_6O_5$ (862.4) MS(FAB) 863.4M+H$^+$

EXAMPLE 2c

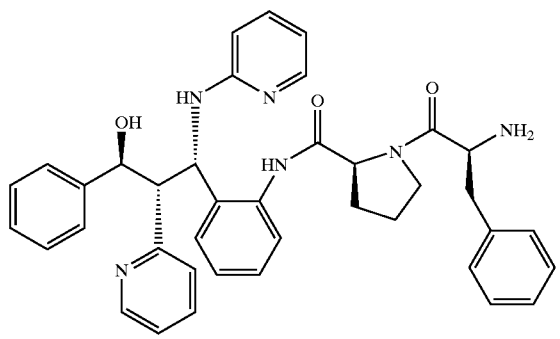

0.8 g (0.93 mmol) of the compound from Example 2b/2 were dissolved in 33 ml of DMF/piperidine 10:1 and the solution was stirred at room temperature for 1 hour. After evaporation, the residue was chromatographed over silica gel (methylene chloride/methanol 19:1, then 9:1).

Yield: 0.35 g (59%).

$C_{39}H_{40}N_6O_3$ (640.3) MS (FAB) 641.3 M+H$^+$

The examples of Table 2 were obtained analogously to Example 1g and Example 2a, starting from Example 1e and Example 1f.

TABLE 2

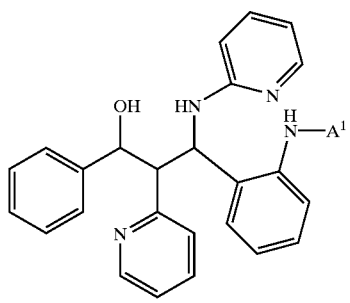

| Example | Amino acid radical $A^1$ | Empirical formula (molecular weight) | MS (FAB) |
|---|---|---|---|
| 3 | Gly | $C_{27}H_{27}N_5O_2$ (453.5) | 454.5 M + H |
| 4 | L-Tyr(t-But) | $C_{38}H_{41}N_5O_3$ (615.7) | 616.7 M + H$^+$ |
| 5 | L-Ser(t-But) | $C_{32}H_{37}N_5O_3$ (539.6) | 540.6 M + H$^+$ |
| 6 | L-Lys(BOC) | $C_{36}H_{44}N_6O_4$ (624.7) | 625.7 M + H$^+$ |
| 7 | L-Tyr | $C_{34}H_{33}N_5O_3$ (559.6) | 560.6 M + H$^+$ |
| 8 | L-Ser | $C_{28}H_{29}N_5O_3$ (483.6) | 484.6 M + H$^+$ |
| 9 | L-Lys | $C_{31}H_{36}N_6O_2$ (524.7) | 525.7 M + H$^+$ |
| 10 | L-Arg(BOC)$_2$ | $C_{41}H_{52}N_8O_6$ (752.9) | 753.9 M + H$^+$ |
| 11 | L-Ornithine(BOC) | $C_{35}H_{42}N_6O_4$ (610.7) | 611.7 M + H$^+$ |

TABLE 2-continued

| Example | Amino acid radical $A^1$ | Empirical formula (molecular weight) | MS (FAB) |
|---|---|---|---|
| 12 | 2,4-Diaminobutyric acid (BOC) | $C_{34}H_{40}N_6O_4$ (596.7) | 597.7 M + H$^+$ |

The examples of Table 3 were obtained analogously to Examples 1h and 2c, starting from Examples 1e and 1f.

TABLE 3

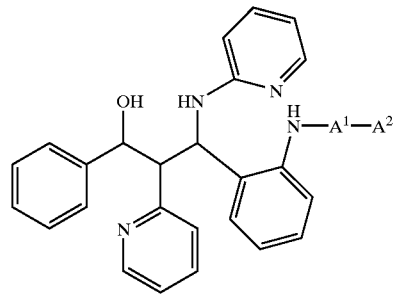

| Example | Amino acid radical $A^1$ | Amino acid radical $A^2$ | Empirical formula (molecular weight) | MS (FAB) |
|---|---|---|---|---|
| 13 (polar) | Gly | Gly | $C_{29}H_{30}N_6O_3$ (510.6) | 511.6 M + H$^+$ |
| 14 (non-polar) | L-Lys (BOC) | L-Lys(BOC) | $C_{47}H_{64}N_8O_7$ (853.1) | 854.1 M + H$^+$ |
| 15 (polar) | L-Lys (BOC) | L-Lys(BOC) | $C_{47}H_{64}N_8O_7$ (853.1) | 854.1 M + H$^+$ |
| 16 (non-polar) | L-Lys (BOC) | L-Ser(BOC) | $C_{43}H_{57}N_7O_6$ (760.0) | 761.0 M + H$^+$ |
| 17 (polar) | L-Lys (BOC) | L-Ser(BOC) | $C_{43}H_{57}N_7O_6$ (760.0) | 761.0 M + H$^+$ |
| 18 (non-polar) | L-Lys (BOC) | L-Arg | $C_{42}H_{56}N_{10}O_5$ (781.0) | 782.0 M + H$^+$ |
| 19 (polar) | L-Lys (BOC) | L-Arg | $C_{42}H_{56}N_{10}O_5$ (781.0) | 782.0 M + H$^+$ |
| 20 | L-Phe | L-Ser(BOC) | $C_{41}H_{46}N_6O_4$ (686.8) | 687.8 M + H$^+$ |
| 21 | L-Phe | L-Phe | $C_{43}H_{42}N_6O_3$ (690.8) | 691.8 M + H$^+$ |
| 22 | L-Phe | L-Lys(BOC) | $C_{45}H_{53}N_7O_5$ (772.0) | 773.0 M + H$^+$ |

The examples of Table 4 were obtained analogously to Example 1g and Example 2a, starting from Example 1e and Example 1f.

TABLE 4

| Example | Formula | Empirical formula | Molecular mass | MS (FAB) |
|---|---|---|---|---|
| 30 | Chiral | C₃₀H₂₈N₆O₄ | 536.6 | 537.6 M + H⁺ |
| 31 | | C₃₀H₂₈N₄O₂ | 476.6 | 477.6 M + H⁺ |
| 32 | | C₃₃H₃₆N₄O₂S₂ | 584.8 | 585.8 M + H⁺ |
| 33 | | C₃₃H₂₉ClN₄O₂ | 549.1 | 550.1 M + H⁺ |

TABLE 4-continued

| Example | Formula | Empirical formula | Molecular mass | MS (FAB) |
|---|---|---|---|---|
| 34 | | $C_{31}H_{28}N_4O_2S$ | 520.7 | 521.7 M + H$^+$ |
| 35 | | $C_{36}H_{36}N_4O_4$ | 588.7 | 589.7 M + H$^+$ |
| 36 | | $C_{35}H_{31}ClN_4O_3$ | 591.1 | 592.1 M + H$^+$ |
| 37 | | $C_{34}H_{32}N_4O_4S$ | 592.7 | 593.7 M + H$^+$ |

TABLE 4-continued

| Example | Formula | Empirical formula | Molecular mass | MS (FAB) |
|---|---|---|---|---|
| 38 | | $C_{34}H_{29}F_3N_4O_2$ | 582.6 | 583.6 M + H+ |
| 39 | | $C_{31}H_{32}N_4O_4$ | 524.6 | 525.6 M + H+ |
| 40 | | $C_{34}H_{38}N_4O_2$ | 534.7 | 535.6 M + H+ |
| 41 | | $C_{31}H_{28}N_4O_2S$ | 520.7 | 521.7 M + H+ |

TABLE 4-continued

| Example | Formula | Empirical formula | Molecular mass | MS (FAB) |
|---|---|---|---|---|
| 42 | | C₃₄H₂₉FN₄O₂ | 544.6 | 545.6 M + H⁺ |
| 43 | | C₃₃H₂₉N₅O₅ | 575.6 | 576.6 M + H⁺ |
| 44 | | C₃₃H₂₉FN₄O₃ | 548.6 | 549.6 M + H⁺ |
| 45 | | C₃₄H₃₂N₄O₃ | 544.7 | 545.6 M + H⁺ |

TABLE 4-continued

| Example | Formula | Empirical formula | Molecular mass | MS (FAB) |
|---|---|---|---|---|
| 46 | | C₃₃H₂₉ClN₄O₂S | 581.1 | 582.1 M + H⁺ |
| 47 | | C₃₅H₂₉N₅O₄ | 583.6 | 584.6 M + H⁺ |
| 48 | | C₃₆H₃₄N₄O₄ | 586.7 | 587.7 M + H⁺ |
| 49 | | C₃₃H₃₇N₅O₄ | 567.7 | 568.7 M + H⁺ |

TABLE 4-continued

| Example | Formula | Empirical formula | Molecular mass | MS (FAB) |
|---|---|---|---|---|
| 50 | | $C_{29}H_{30}N_4O_3$ | 482.6 | 483.6 M + H⁺ |
| 51 | | $C_{34}H_{30}N_4O_3$ | 542.6 | 543.6 M + H⁺ |
| 52 | | $C_{35}H_{32}N_4O_4$ | 572.7 | 573.7 M + H⁺ |
| 53 | | $C_{32}H_{28}N_4O_2S$ | 532.7 | 533.7 M + H⁺ |

TABLE 4-continued

| Example | Formula | Empirical formula | Molecular mass | MS (FAB) |
|---|---|---|---|---|
| 54 | | $C_{38}H_{32}N_4O_2$ | 576.7 | 577.7 M + H+ |
| 55 | | $C_{36}H_{32}N_4O_4$ | 584.7 | 585.7 M + H+ |
| 56 | | $C_{31}H_{28}N_6O_2S$ | 548.7 | 549.7 M + H+ |
| 57 | | $C_{31}H_{30}N_4O_4$ | 522.6 | 523.6 M + H+ |

TABLE 4-continued

| Example | Formula | Empirical formula | Molecular mass | MS (FAB) |
|---|---|---|---|---|
| 58 | | $C_{31}H_{30}N_4O_2$ | 490.6 | 491.6 M + H$^+$ |
| 59 | | $C_{34}H_{32}N_4O_4$ | 560.7 | 561.7 M + H$^+$ |
| 60 | | $C_{33}H_{34}N_4O_2$ | 518.7 | 519.7 M + H$^+$ |
| 61 | | $C_{32}H_{30}N_6O_2S$ | 562.7 | 563.7 M + H$^+$ |

TABLE 4-continued

| Example | Formula | Empirical formula | Molecular mass | MS (FAB) |
| --- | --- | --- | --- | --- |
| 62 | | C₃₀H₂₇N₅O₂ | 489.6 | 490.6 M + H⁺ |
| 63 | | C₃₄H₃₀Cl₂N₄O₂S | 629.6 | 530.6 M + H⁺ |
| 64 | | C₃₅H₃₃N₅O₄ | 587.7 | 588.7 M + H⁺ |
| 65 | | C₃₁H₂₇N₅O₅S | 581.7 | 582.6 M + H⁺ |

TABLE 4-continued

| Example | Formula | Empirical formula | Molecular mass | MS (FAB) |
|---|---|---|---|---|
| 66 | | $C_{35}H_{36}N_4O_3S$ | 592.8 | 593.8 M + H⁺ |
| 67 | | $C_{32}H_{27}F_3N_4O_4S$ | 620.6 | 521.6 M + H⁺ |
| 68 | | $C_{39}H_{37}N_7O_3S$ | 683.8 | 584.8 M + H⁺ |
| 69 | | $C_{35}H_{38}N_4O_4S$ | 610.8 | 611.6 M + H⁺ |

TABLE 4-continued

| Example | Formula | Empirical formula | Molecular mass | MS (FAB) |
|---|---|---|---|---|
| 70 | | $C_{34}H_{29}N_5O_3S$ | 587.7 | 588.7 M + H⁺ |
| 71 | | $C_{33}H_{31}ClN_4O_3S$ | 599.2 | 600.2 M + H⁺ |
| 72 | | $C_{34}H_{34}N_4O_3S$ | 578.7 | 579.7 M + H⁺ |
| 73 | | $C_{31}H_{27}FN_4O_3S$ | 554.6 | 555.6 M + H⁺ |

TABLE 4-continued

| Example | Formula | Empirical formula | Molecular mass | MS (FAB) |
|---|---|---|---|---|
| 74 | | C₃₁H₂₆Cl₂N₄O₄S | 621.5 | 522.5 M + H⁺ |
| 75 | | C₃₁H₂₆N₆O₇S | 626.6 | 627.6 M + H⁺ |
| 76 | | C₃₁H₂₆Cl₂N₄O₃S | 605.5 | 606.5 M + H⁺ |
| 77 | | C₂₈H₃₀N₄O₃S | 502.6 | 503.6 M + H⁺ |

TABLE 4-continued

| Example | Formula | Empirical formula | Molecular mass | MS (FAB) |
|---|---|---|---|---|
| 78 | | $C_{33}H_{26}F_6N_4O_3S$ | 672.6 | 573.6 M + H⁺ |
| 79 | | $C_{32}H_{29}BrN_4O_4S$ | 645.6 | 646.6 M + H⁺ |
| 80 | | $C_{41}H_{56}N_4O_3S$ | 685.0 | 686.0 M + H⁺ |
| 81 | | $C_{29}H_{25}BrN_4O_3S_2$ | 621.6 | 622.6 M + H⁺ |
| 82 | | $C_{29}H_{25}ClN_4O_3S_2$ | 577.1 | 578.1 M + H⁺ |

TABLE 4-continued

| Example | Formula | Empirical formula | Molecular mass | MS (FAB) |
|---|---|---|---|---|
| 83 | | $C_{39}H_{42}N_4O_4S$ | 662.9 | 663.9 M + H⁺ |
| 84 | | $C_{35}H_{30}N_4O_5S_3$ | 682.8 | 683.8 M + H⁺ |
| 85 | | $C_{33}H_{30}N_4O_5S$ | 594.7 | 595.7 M + H⁺ |
| 86 | | $C_{33}H_{40}N_4O_3S$ | 572.8 | 573.8 M + H⁺ |

TABLE 4-continued

| Example | Formula | Empirical formula | Molecular mass | MS (FAB) |
|---|---|---|---|---|
| 87 | | $C_{35}H_{36}N_4O_4S$ | 608.8 | 609.8 M + H⁺ |
| 88 | | $C_{35}H_{30}N_4O_3S$ | 586.7 | 587.7 M + H⁺ |
| 89 | | $C_{37}H_{35}N_5O_3S$ | 629.8 | 630.8 M + H⁺ |
| 90 | | $C_{32}H_{26}F_3N_5O_5S$ | 649.6 | 650.6 M + H⁺ |

TABLE 4-continued

| Example | Formula | Empirical formula | Molecular mass | MS (FAB) |
|---|---|---|---|---|
| 91 | | C₃₂H₂₈N₄O₅S | 580.7 | 581.7 M + H⁺ |
| 92 | | C₃₆H₃₈N₄O₃S | 606.8 | 607.8 M + H⁺ |
| 93 | | C₃₁H₃₀N₆O₄S₂ | 614.7 | 615.7 M + H⁺ |
| 94 | | C₃₂H₃₀N₄O₅S₂ | 614.7 | 615.7 M + H⁺ |

EXAMPLE 95

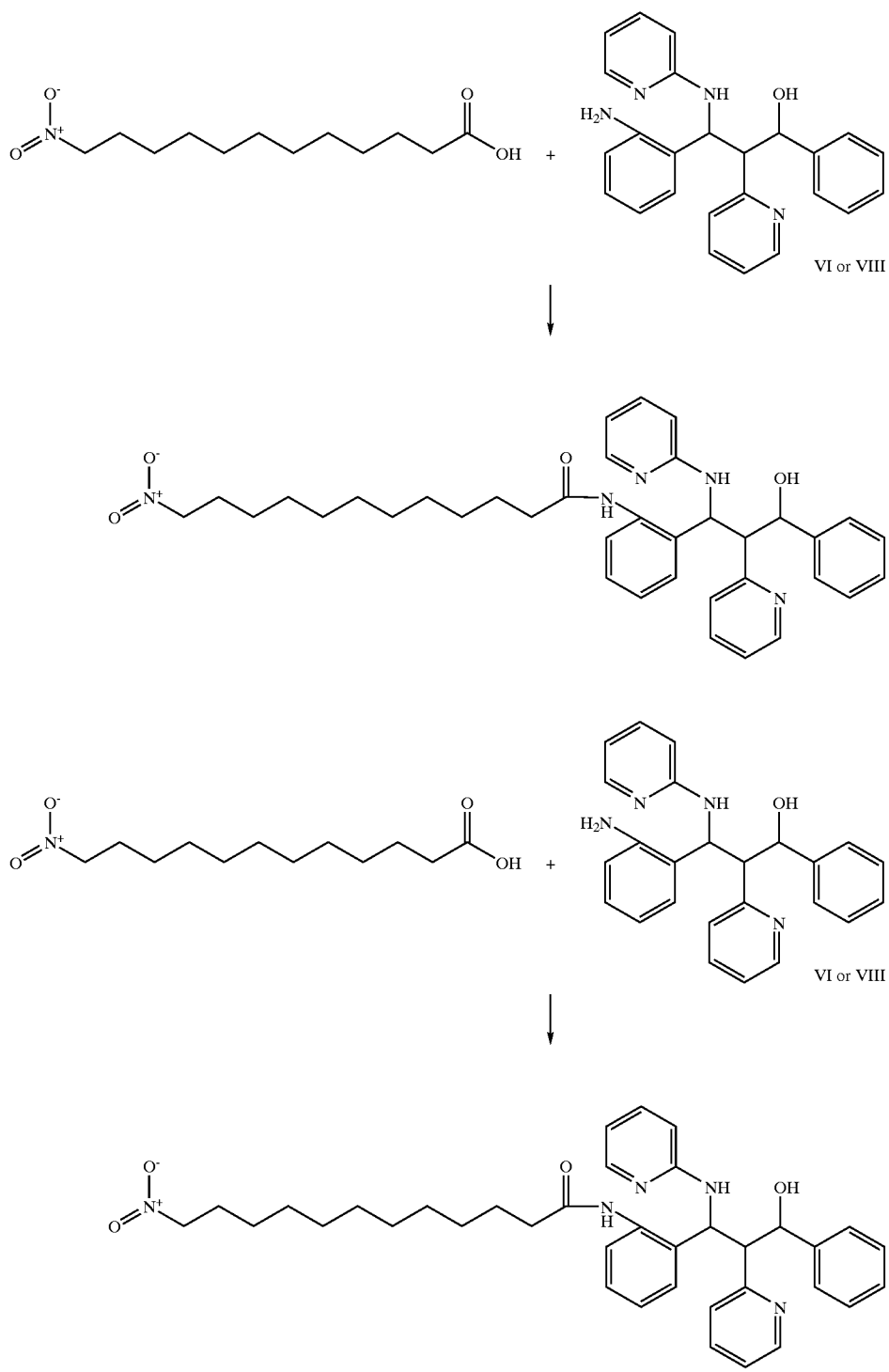

1.6 g of the amine of formula VI or VIII and 0.98 g of 12-nitrododecanoic acid were dissolved in 30 ml of dimethylformamide. 1.6 g of O-((ethoxycarbonyl)cyanomethyleneamino)-N,N,N',N'-tetramethyluronium tetrafluoroborate (TOTU), 0.6 g of ethyl (hydroxyimino)cyanoacetate and 1.6 ml of N-ethylmorpholine were added and the mixture was stirred at room temperature for approximately 2 hours. When the reaction had ended (as indicated by thin layer chromatography), the reaction mixture was extracted by stirring with 500 ml of water and 200 ml of methylene chloride and the organic phase was separated off, dried and concentrated in vacuo. After column chromatography (CC, SiO$_2$, ethyl acetate/n-heptane=2:1), the amide was obtained as a viscous oil. Empirical formula:

$C_{37}H_{45}N_5O_4$; (623.4); MS(FAB): 624.4 M+H$^+$

EXAMPLE 96

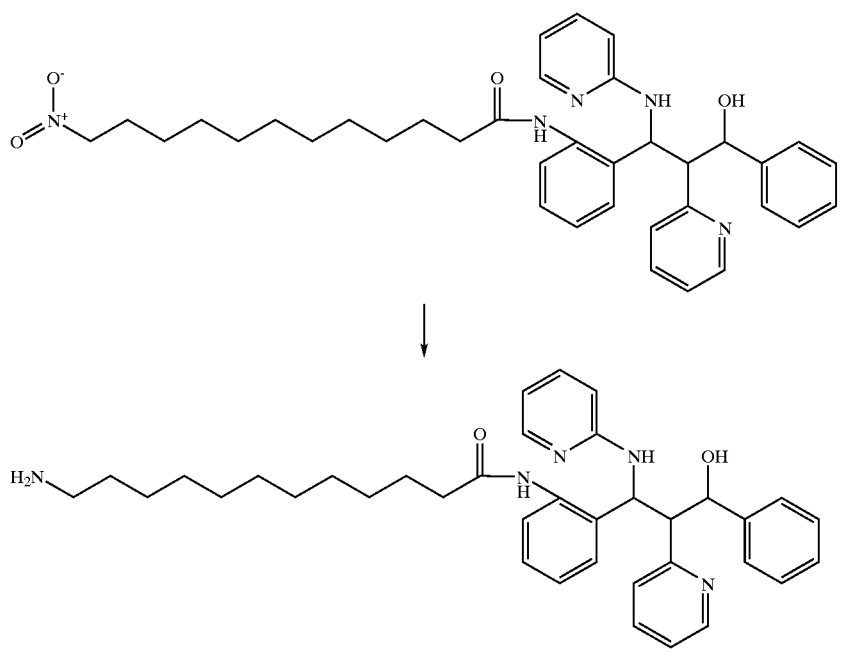

2.2 g of the amide were dissolved in 200 ml of ethanol and, after addition of a catalytic amount of Raney nickel (aqueous suspension), hydrogenation was carried out in a duck-shaped shaking vessel under normal pressure at room temperature. The mixture was filtered off with suction over a clarifying layer and concentrated to give, after CC (SiO$_2$, methylene chloride/methanol/ammonia=90:10:1) Example 96. Empirical formula: C$_{37}$H$_{47}$N$_5$O$_2$ (593.8) MS(FAB): 595 M+H$^+$

EXAMPLE 97

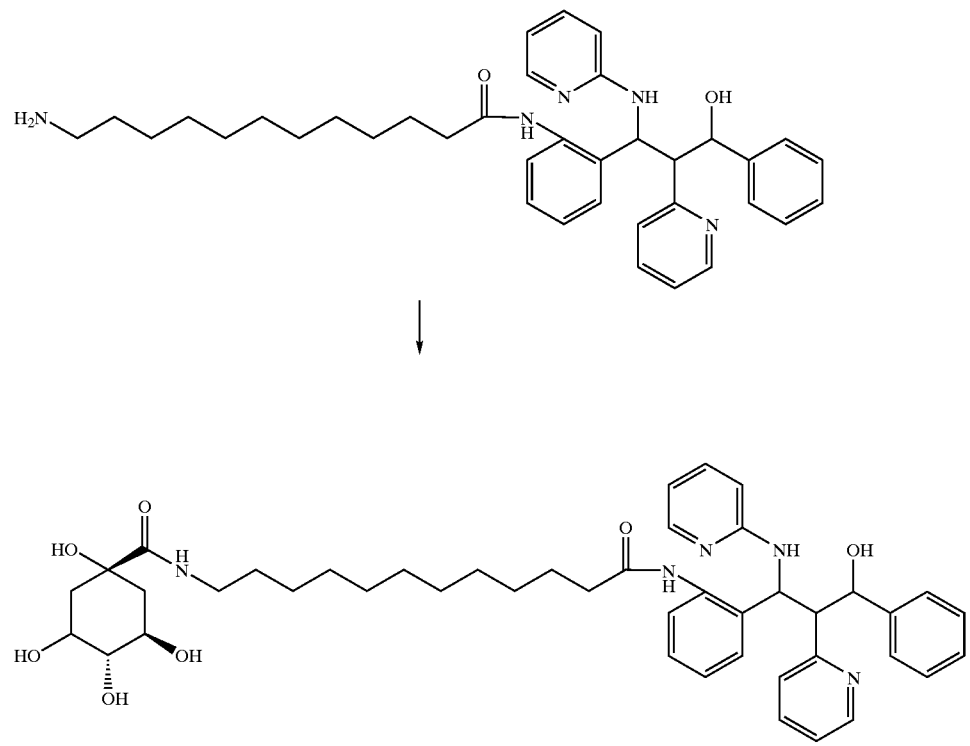

1.2 g of Example 96, 390 mg of China acid and 330 mg of N-hydroxy-benzotriazole were dissolved in 100 ml of tetrahydrofuran, and 500 mg of dicyclohexylcarbodiimide were added. The mixture was stirred at room temperature for 17 hours, filtered and concentrated. The residue was taken up in about 500 ml of ethyl acetate, extracted by shaking successively with NaHCO₃ solution, 2N citric acid, NaHCO₃ solution and water, and then dried and concentrated. After column filtration (ethyl acetate/methanol =9:1), Example 97 was obtained, melting point 95° C. Empirical formula: $C_{44}H_{47}N_5O_7$ (768),

MS(FAB): 768.4 M+H⁺

EXAMPLE 98

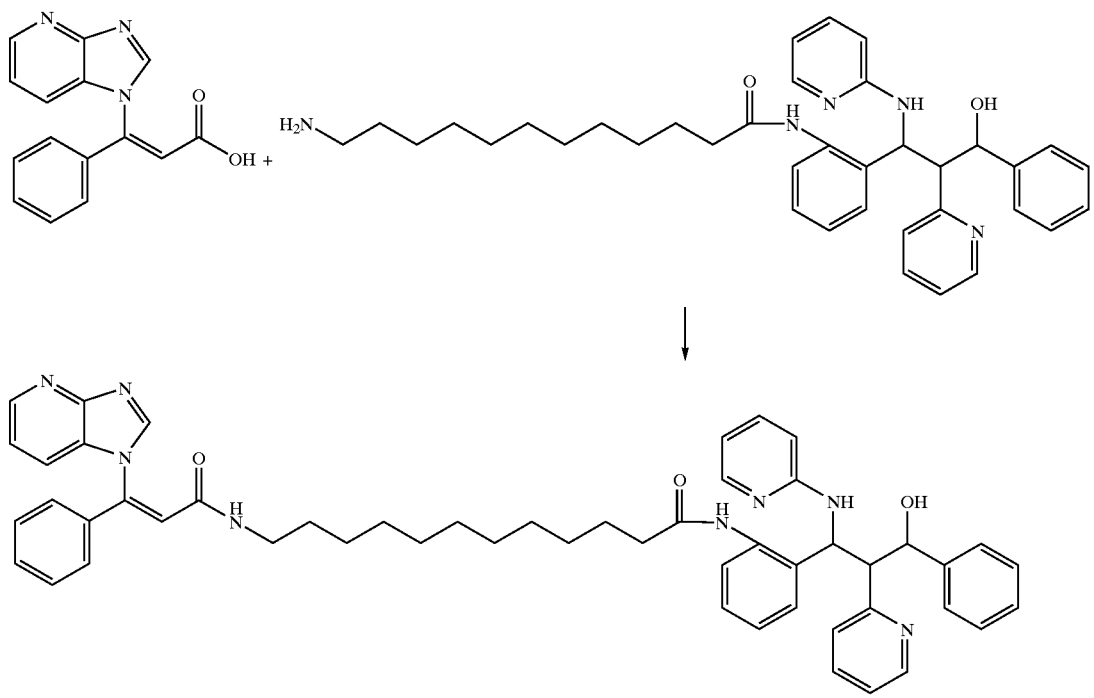

593 mg of Example 96 and 265 mg of the carboxyl acid shown above were dissolved in 20 ml of DMF. 600 mg of TOTU, 300 mg of ethyl hydroxy-imino-cyanoacetate and 1 ml of N-ethylmorpholine were added and the mixture was stirred at room temperature for about 2 hours. When the reaction had ended (as indicated by thin layer chromatography), ethyl acetate was added and the mixture was washed in each case twice with water and NaHCO₃ solution, the organic phase was concentrated and the residue was purified by column chromatography (SiO₂, ethyl acetate/methanol=9:1). The amide Example 4 of melting point 105° C. was obtained. Empirical formula: $C_{52}H_{56}N_8O_3$ (840.5); MS: 842 (M+H⁺)

The following substances were prepared analogously to Example 98 from the amine of Example 96 and the corresponding carboxylic acid:

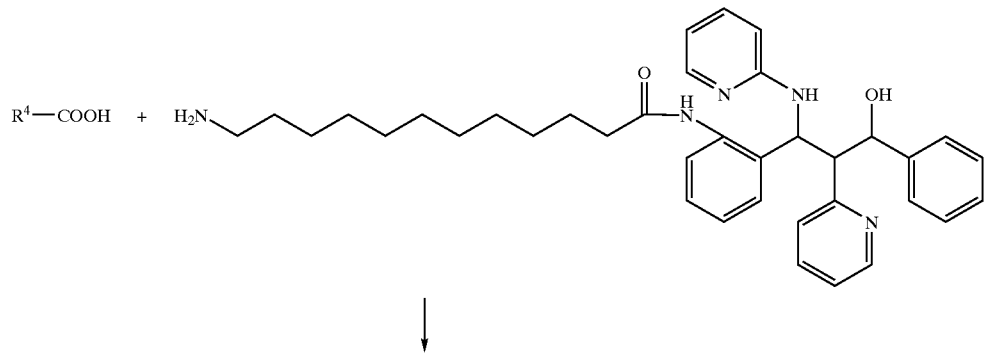

-continued
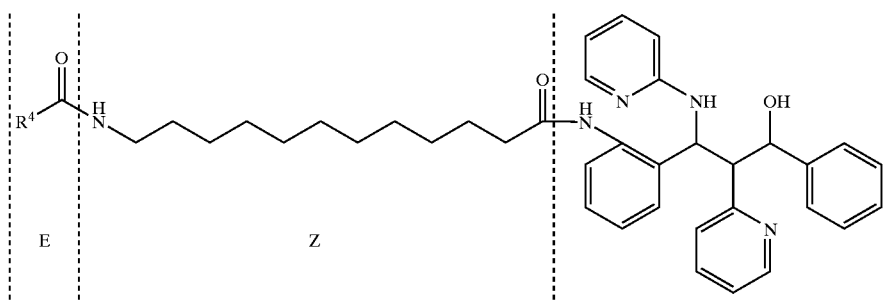
E | Z
TABLE 5
| Example | R⁴—COOH | Empirical formula (mass number) | MS (FAB) |
|---|---|---|---|
| 99 | (11-aminoundecanoic acid derivative with cyanoacetamide) | $C_{40}H_{48}N_6O_3$ 660.4 | 661.5 (M + H⁺) |
| 100 | (succinic acid N',N'-dimethylhydrazide) | $C_{43}H_{57}N_7O_4$ 735.5 | 737 (M + H⁺) |
| 101 | (2,2-bis(hydroxymethyl)propionic acid) | $C_{42}H_{55}N_5O_5$ 709.4 | 711 (M + H⁺) |
| 102 | (difluoroacetic acid) | $C_{39}H_{47}F_2N_5O_3$ 671.4 | 673 (M + H⁺) |
| 103 | (caffeic acid) | $C_{46}H_{53}N_5O_5$ 755.4 | 757 (M + H⁺) |
| 104 | (2-aminonicotinic acid) | $C_{43}H_{51}N_7O_3$ 713.4 | 715 (M + H⁺) |

TABLE 5-continued

| Example | R⁴—COOH | Empirical formula (mass number) | MS (FAB) |
|---|---|---|---|
| 105 | 3,4-diaminobenzoic acid | C₄₄H₅₃N₇O₃ 727.4 | 729 (M + H⁺) |
| 106 | (S)-5-oxotetrahydrofuran-2-carboxylic acid | C₄₂H₅₁N₅O₅ 705.4 | 707 (M + H⁺) |
| 107 | 4-(semicarbazono)pentanoic acid | C₄₃H₅₆N₈O₄ 748.4 | 750 (M + H⁺) |
| 108 | phthalamic acid | C₄₅H₅₂N₆O₄ 740.4 | 741 (M + H⁺) |
| 109 | N-acetylglycylglycine | C₄₃H₅₅N₇O₅ 749.4 | 751 (M + H⁺) |
| 110 | (methylsulfonyl)acetic acid | C₄₀H₅₁N₅O₅S 713.4 | 715 (M + H⁺) |
| 111 | adenosine-5'-carboxylic acid | C₄₇H₅₆N₁₀O₆ 856.4 | 858 (M + H⁺) |
| 112 | (Z)-2-(2-aminothiazol-4-yl)-2-(hydroxyimino)acetic acid | C₄₂H₅₀N₈O₄S 762.4 | 764 (M + H⁺) |
| 113 | monoethyl maleate | C₄₃H₅₃N₅O₅ 719.4 | 721 (M + H⁺) |

TABLE 5-continued

| Example | R⁴—COOH | Empirical formula (mass number) | MS (FAB) |
|---|---|---|---|
| 114 | (hydantoin/dihydrouracil carboxylic acid structure) | $C_{42}H_{51}N_7O_5$ 733.4 | 735 (M + H⁺) |
| 115 | (2-thioxoimidazolidinone acetic acid structure) | $C_{43}H_{53}N_7O_4S$ 763.4 | 765 (M + H⁺) |
| 116 | (pyrrolidinone with pyridyl and carboxyl structure) | $C_{48}H_{57}N_7O_4$ 795.5 | 797 (M + H⁺) |
| 117 | (urocanic acid structure) | $C_{43}H_{51}N_7O_3$ 713.4 | 715 (M + H⁺) |
| 118 | (caffeine-N-acetic acid / theophylline acetic acid structure) | $C_{46}H_{55}N_9O_5$ 813.4 | 815 (M + H⁺) |
| 119 | (imidazole acetic acid structure) | $C_{42}H_{51}N_7O_3$ 701.4 | 703 (M + H⁺) |
| 120 | (sinapic acid structure) | $C_{48}H_{57}N_5O_6$ 799.4 | 801 (M + H⁺) |
| 121 | (N,N-dimethylsuccinamic acid structure) | $C_{43}H_{56}N_6O_4$ 720.4 | 722 (M + H⁺) |

TABLE 5-continued

| Example | R⁴—COOH | Empirical formula (mass number) | MS (FAB) |
|---|---|---|---|
| 122 | 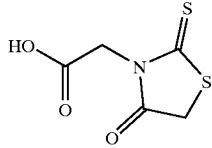 | $C_{42}H_{50}N_6O_4S_2$ 766.3 | 768 (M + H⁺) |
| 123 | 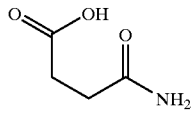 | $C_{41}H_{52}N_6O_4$ 692.4 | 694 (M + H⁺) |
| 124 | 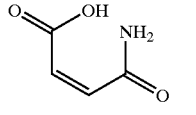 | $C_{41}H_{50}N_6O_4$ 690.4 | 692 (M + H⁺) |
| 125 | 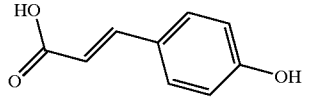 | $C_{46}H_{53}N_5O_4$ 739.4 | 741 (M + H⁺) |

The examples of Tables 6 and 7 were obtained analogously to Process A, Equation 2 (see page 13).

TABLE 6

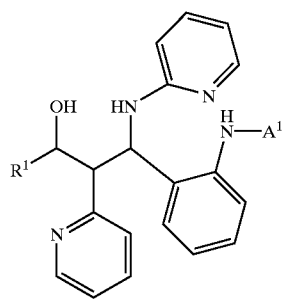

| Example | R¹ | Amino acid radical A¹ | Empirical formula (molecular weight) | MS |
|---|---|---|---|---|
| 133 | 3,5-Dimethyl-isoxazol-4-yl | D-Lys(Boc) | $C_{35}H_{45}N_7O_5$ (643.8) | 644.4 (FAB), M + H⁺ |
| 134 | 2,4-Dimethyl-thiazol-5-yl | D-Lys(Boc) | $C_{35}H_{45}N_7O_4S$ (659.9) | 660.4 (ESI), M + H⁺ |

TABLE 6-continued

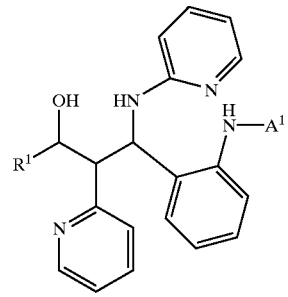

| Example | R¹ | Amino acid radical A¹ | Empirical formula (molecular weight) | MS |
|---|---|---|---|---|
| 135 | 2,5-Dimethyl-oxazol-4-yl | D-Lys(Boc) | $C_{35}H_{45}N_7O_5$ (643.8) | 644.4 (FAB), M + H⁺ |

TABLE 7

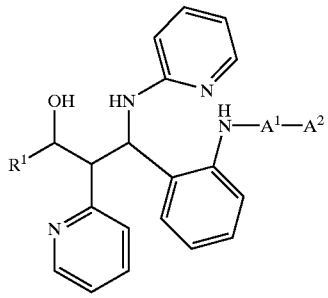

| Example | R[1] | Amino acid radical A[1] | Amino acid radical A[2] | Empirical formula (molecular weight) | MS (FAB) |
|---|---|---|---|---|---|
| 143 (highly non-polar) | 3,5-Dimethyl-isoxazolyl-4-yl | L-Proline | L-Phenyl-alanine | $C_{38}H_{41}N_7O_4$ (659.8) | 660.3 (ESI), M + H[+] |
| 144 (highly non-polar) | 3,5-Dimethyl-isoxazolyl-4-yl | D-Lys(Boc) | D-Lys(Boc) | $C_{46}H_{65}N_9O_8$ (872.1) | 772.4 (FAB), M + H[+] |
| 145 (highly non-polar) | 2,5-Dimethyl-oxazol-4-yl | D-Lys(Boc) | D-Lys(Boc) | $C_{46}H_{65}N_9O_8$ (872.1) | 772.5 (FAB), M + H[+] |
| 146 (highly non-polar | 5-Methyl-isoxazol-3-yl | D-Lys(Boc) | D-Lys(Boc) | $C_{45}H_{63}N_9O_8$ (858.1) | 858.5 (FAB), M + H[+] |
| 147 (highly non-polar) | 2,4-Dimethyl-thiazol-5-yl | D-Lys(Boc) | D-Lys(Boc) | $C_{46}H_{65}N_9O_7S$ (888.2) | 888.6 (ESI) M + H[+] |
| 148 non-polar | 2,4-Dimethyl-thiazol-5-yl | D-Lys(Boc) | D-Lys(Boc) | $C_{46}H_{65}N_9O_7S$ (888.2) | 888.4 (FAB) M + H[+] |
| 149 (moderately polar) | 2,4-Dimethyl-thiazol-5-yl | D-Lys(Boc) | D-Lys(Boc) | $C_{46}H_{65}N_9O_7S$ (888.2) | 888.6 (ESI) M + H[+] |
| 150 S983499 (polar) | 2,4-Dimethyl-thiazol-5-yl | D-Lys(Boc) | D-Lys(Boc) | $C_{46}H_{65}N_9O_7S$ (888.2) | 888.4 (FAB) M + H[+] |
| 151 (highly non-polar) | 2,4-Dimethyl-thiazol-5-yl | D-Lys(Boc) | L-Phenyl-alanine | $C_{44}H_{54}N_8O_5S$ (807.0) | 807.5 (ESI) M + H[+] |
| 32 (highly non-polar) | 2,4-Dimethyl-thiazol-5-yl | L-Proline | L-Phenyl-alanine | $C_{38}H_{41}N_7O_3S$ (675.9) | 676.4 (FAB) M + H[+] |

We claim:

1. A compound of the formula (I), or a salt thereof,

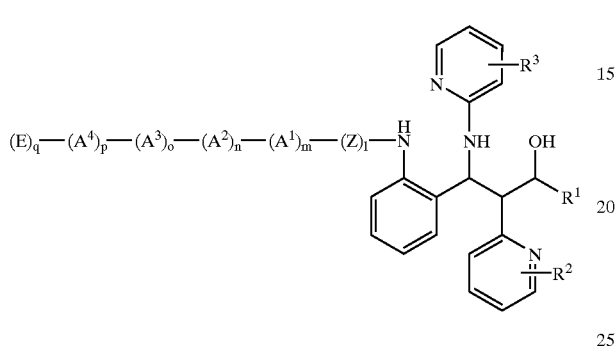

in which

Z is
—NH—($C_1$–$C_{16}$-alkyl)-(C=O)—;
—(C=O)—($C_1$–$C_{16}$-alkyl)-(C=O)—; or
—(C=O)-phenyl-(C=O)—;

$A^1$, $A^2$, $A^3$, $A^4$, each independently of one another is the D- or L-form of alanine, glycine, proline, cysteine, histidine, glutamine, aspartic acid, isoleucine, arginine, glutamic acid, lysine, serine, phenylalanine, leucine, threonine, tryptophan, methionine, valine, tyrosine, asparagine, 2-aminoadipic acid, 2-aminoisobutyric acid, 3-aminoadipic acid, 3-aminoisobutyric acid, beta-alanine, 2-aminopimelic acid, 2-aminobutyric acid, 2,4-diaminobutyric acid, 4-aminobutyric acid, desmosine, piperidic acid, 2,2-diaminopimelic acid, 6-aminocaproic acid, 2,3-diaminopropionic acid, 2-aminoheptanoic acid, N-ethylglycine, 2-(2-thienyl)-glycine, 3-(2-thienyl)-alanine, penicillamine, sarcosine, N-ethylasparagine, N-methylisoleucine, hydroxylysine, 6-N-methyllysine, allo-hydroxylysine, N-methylvaline, 3-hydroxyproline, norvaline, 4-hydroxyproline, norleucine, isodesmosine, ornithine, allo-isoleucine, 3-(2-naphthyl)alanine, azaglycine, N-cyclohexylglycine, or 2,4-diaminobutyric acid, E is —$SO_2$—$R^4$, —CO—$R^4$;

R is phenyl, thiazolyl, oxazolyl, thienyl, thiophenyl, furanyl, pyridyl, or pyrimidyl, wherein the rings are unsubstituted, or are substituted up to 3 times by F, Cl, Br, OH, $CF_3$, $NO_2$, CN, $OCF_3$, —($C_1$–$C_6$)-alkyl, —O—($C_1$–$C_6$)-alkyl, —S—($C_1$–$C_6$)-alkyl, —SO—($C_1$–$C_6$)-alkyl, —$SO_2$—($C_1$–$C_6$)-alkyl, —($C_1$–$C_6$)-alkyl, —($C_3$–$C_6$)-cycloalkyl, —COOH, —COO($C_1$–$C_6$)alkyl, —COO($C_3$–$C_6$)cycloalkyl, —$CONH_2$, —CONH($C_1$–$C_6$)alkyl, —CON[($C_1$–$C_6$)alkyl]$_2$, —CONH($C_3$–$C_6$)cycloalkyl, —$NH_2$, —NH—CO—($C_1$–$C_6$)-alkyl, or —NH—CO-phenyl;

$R^2$ is H, —OH, —$CH_2OH$, or —OMe;

$R^3$ is H, F, methyl, or —OMe;

$R^4$ is —($C_1$–$C_{16}$-alkyl), —($C_0$–$C_{16}$-alkylene)-$R^5$, —(C=O)—($C_0$–$C_{16}$-alkylene)-$R^5$, —(C=O)—($C_0$–$C_{16}$-alkylene)-NH—$R^5$, —($C_1$–$C_8$-alkenylene)-$R^5$, —($C_1$–$C_8$-alkynyl), —($C_1$–$C_4$-alkylene)-S(O)$_r$—$R^5$, —($C_1$–$C_4$-alkylene)-O—$R^5$, or —($C_1$–$C_4$-alkylene)-NH—$R^5$;

$R^5$ is —COO—$R^6$, —(C=O)—$R^6$, —($C_1$–$C_6$-alkylene)-$R^7$, —($C_1$–$C_6$-alkenylene)-$R^7$, —($C_1$–$C_7$)-cycloalkyl, phenyl, naphthyl, thienyl, thiophenyl, furanyl, pyridyl, pyrimidyl, dihydropyrimidine-2,4-dion-6-yl, chromanyl, phthalimidoyl, or thiazolyl, wherein the rings are unsubstituted, or are substituted up to 3 times by F, Cl, Br, —OH, —$CF_3$, —$NO_2$, —CN, —$OCF_3$, —($C_1$–$C_6$)-alkyl, —O—($C_1$–$C_6$)-alkyl, —S—($C_1$–$C_6$)-alkyl, —SO—($C_1$–$C_6$)-alkyl, —$SO_2$—($C_1$–$C_6$)-alkyl, —($C_1$–$C_6$)-alkyl, —($C_3$–$C_6$)-cycloalkyl, —COOH, —COO($C_1$–$C_6$)alkyl, —COO($C_3$–$C_6$)cycloalkyl, —$CONH_2$, —CONH($C_1$–$C_6$)alkyl, —CON[($C_1$–$C_6$)alkyl]$_2$, —CONH($C_3$–$C_6$)cycloalkyl, —$NH_2$, —NH—CO—($C_1$–$C_6$)-alkyl, —NH—CO-phenyl, or pyridyl;

$R^6$ is H or —($C_1$–$C_6$)alkyl;

$R^7$ is H, —($C_1$–$C_7$)-cycloalkyl, phenyl, naphthyl, thienyl, thiophenyl, furanyl, pyridyl, pyrimidyl, dihydropyrimidine-2,4-dion-6-yl, chromanyl, phthalimidoyl, or thiazolyl, wherein the rings are unsubstituted, or are substituted up to 3 times by F, Cl, Br, OH, $CF_3$, $NO_2$, CN, $OCF_3$, —($C_1$–$C_6$)-alkyl, —O—($C_1$–$C_6$)-alkyl, —S—($C_1$–$C_6$)-alkyl, —SO—($C_1$–$C_6$)-alkyl, —$SO_2$—($C_1$–$C_6$)-alkyl, —($C_1$–$C_6$)-alkyl, —($C_3$–$C_6$)-cycloalkyl, —COOH, —COO($C_1$–$C_6$)alkyl, —COO($C_3$–$C_6$)cycloalkyl, —$CONH_2$, —CONH($C_1$–$C_6$)alkyl, —CON[($C_1$–$C_6$)alkyl]$_2$, —CONH($C_3$–$C_6$)cycloalkyl, —$NH_2$, —NH—CO—($C_1$–$C_6$)-alkyl, or —NH—CO-phenyl;

l, q, m, n, o, p each independently of one another is 0 or 1, where l+q+m+n+o+p is greater than or equal to 1;

r is 0, 1, or 2;

with the proviso that in formula (I), when $R^1$ is unsubstituted phenyl, $R^2$ is H, $R^3$ is H, and l, m, n, o, and p are all zero, then $R^4$ is other than —$CH_3$ or —$C(CH_3)_3$.

2. A compound of the formula (I) or salt thereof as claimed in claim 1, wherein

Z is
—NH—($C_1$–$C_{16}$-alkyl)-(C=O)—,
—(C=O)—($C_1$–$C_{16}$-alkyl)-(C=O)—, or
—(C=O)-phenyl-(C=O)—;

$A^1$, $A^2$, $A^3$, $A^4$ each independently of one another is the D- or L-form of alanine, glycine, proline, cysteine, histidine, glutamine, aspartic acid, isoleucine, arginine, glutamic acid, lysine, serine, phenylalanine, leucine, threonine, tryptophan, methionine, valine, tyrosine, asparagine, 2-aminoadipic acid, 2-aminoisobutyric acid, 3-aminoadipic acid, 3-aminoisobutyric acid, beta-alanine, 2-aminopimelic acid, 2-aminobutyric acid, 2,4-diaminobutyric acid, 4-aminobutyric acid, desmosine, piperidic acid, 2,2-diaminopimelic acid, 6-aminocaproic acid, 2,3-diaminopropionic acid, 2-aminoheptanoic acid, N-ethylglycine, 2-(2-thienyl)-glycine, 3-(2-thienyl)-alanine, penicillamine, sarcosine, N-ethylasparagine, N-methylisoleucine, hydroxylysine, 6-N-methyllysine, allo-hydroxylysine, N-methylvaline, 3-hydroxyproline, norvaline, 4-hydroxyproline, norleucine, isodesmosine, ornithine, allo-isoleucine, 3-(2-naphthyl)alanine, azaglycine, N-cyclohexylglycine, or 2,4-diaminobutyric acid, E is —SO$_2$—R$^4$, or —CO—R$^4$;

R$^1$ is phenyl, thiazolyl, oxazolyl, thienyl, thiophenyl, furanyl, pyridyl, or pyrimidyl, wherein the rings are unsubtituted, or are substituted up to 3 times by F, Cl, Br, —OH, —CF$_3$, —NO$_2$, —CN, —OCF$_3$, —(C$_1$-C$_6$)-alkyl, —O—(C$_1$-C$_6$)-alkyl, —S—(C$_1$-C$_6$)-alkyl, —SO—(C$_1$-C$_6$)-alkyl, —SO$_2$—(C$_1$-C$_6$)-alkyl, —(C$_1$-C$_6$)-alkyl, —(C$_3$-C$_6$)-cycloalkyl, —COOH, —COO(C$_1$-C$_6$)alkyl, —COO(C$_3$-C$_6$)cycloalkyl, —CONH$_2$, —CONH(C$_1$-C$_6$)alkyl, —CON[(C$_1$-C$_6$)alkyl]$_2$, —CONH(C$_3$-C$_6$)cycloalkyl, —NH$_2$, —NH—CO—(C$_1$-C$_6$)-alkyl, or —NH—CO-phenyl;

R$^2$ is H, —OH, —CH$_2$OH, or —OMe;

R$^3$ is H, F, methyl, or —OMe;

R$^4$ is —(C$_1$-C$_{16}$-alkyl), —(C$_0$-C$_{16}$-alkylene)-R$^5$, —(C=O)—(C$_0$-C$_{16}$-alkylene)-R$^5$, —(C=O)—(C$_0$-C$_{16}$-alkylene)-NH—R$^5$, —(C$_1$-C$_8$-alkenylene)-R$^5$, —(C$_1$-C$_8$-alkynyl), —(C$_1$-C$_4$-alkylene)-S(O)$_r$—R$^5$, —(C$_1$-C$_4$-alkylene)-O—R$^5$, or —(C$_1$-C$_4$-alkylene)-NH—R$^5$;

R$^5$ is —COO—R$^6$, —(C=O)—R$^6$, —(C$_1$-C$_6$-alkylene)-R$^7$, —(C$_1$-C$_6$-alkenylene)-R$^7$, —(C$_1$-C$_7$)-cycloalkyl, phenyl, naphthyl, thienyl, thiophenyl, furanyl, pyridyl, pyrimidyl, dihydropyrimidine-2,4-dion-6-yl, chromanyl, phthalimidoyl, or thiazolyl, wherein the rings are unsubstituted, or are substituted up to 3 times by F, Cl, Br, —OH, —CF$_3$, —NO$_2$, —CN, —OCF$_3$, —(C$_1$-C$_6$)-alkyl, —O—(C$_1$-C$_6$)-alkyl, —S—(C$_1$-C$_6$)-alkyl, —SO—(C$_1$-C$_6$)-alkyl, —SO$_2$—(C$_1$-C$_6$)-alkyl, —(C$_1$-C$_6$)-alkyl, —(C$_3$-C$_6$)-cycloalkyl, —COOH, —COO(C$_1$-C$_6$)alkyl, —COO(C$_3$-C$_6$)cycloalkyl, —CONH$_2$, —CONH(C$_1$-C$_6$)alkyl, —CON[(C$_1$-C$_6$)alkyl]$_2$, —CONH(C$_3$-C$_6$)cycloalkyl, —NH$_2$, —NH—CO—(C$_1$-C$_6$)-alkyl, —NH—CO-phenyl, or pyridyl;

R$^6$ is H, or —(C$_1$-C$_6$)alkyl;

R$^7$ is H, —(C$_1$-C$_7$)-cycloalkyl, phenyl, naphthyl, thienyl, thiophenyl, furanyl, pyridyl, pyrimidyl, dihydropyrimidine-2,4-dion-6-yl, chromanyl, phthalimidoyl, or thiazolyl, wherein the rings are unsubstituted, or are substituted up to 3 times by F, Cl, Br, —OH, —CF$_3$, —NO$_2$, —CN, —OCF$_3$, —(C$_1$-C$_6$)-alkyl, —O—(C$_1$-C$_6$)-alkyl, —S—(C$_1$-C$_6$)-alkyl, —SO—(C$_1$-C$_6$)-alkyl, —SO$_2$—(C$_1$-C$_6$)-alkyl, —(C$_1$-C$_6$)-alkyl, —(C$_3$-C$_6$)-cycloalkyl, —COOH, —COO(C$_1$-C$_6$)alkyl, —COO(C$_3$-C$_6$)cycloalkyl, —CONH$_2$, —CONH(C$_1$-C$_6$)alkyl, —CON[(C$_1$-C$_6$)alkyl]$_2$, —CONH(C$_3$-C$_6$)cycloalkyl, —NH$_2$, —NH—CO—(C$_1$-C$_6$)-alkyl, or —NH—CO-phenyl;

l is 0 or 1;

m, n are 0;

o is 1;

p is 0 or 1;

q is 0 or 1; and r is 0, 1, or 2.

3. A compound of formula (I), or a salt thereof, as claimed in claim 1, wherein:

Z is
—NH—(C$_1$-C$_{12}$-alkyl)-(C=O)—,
—(C=O)—(C$_1$-C$_{12}$-alkyl)-(C=O)—, or
—(C=O)-phenyl-(C=O)—;

A$^1$, A$^2$, A$^3$, A$^4$ each independently of one another is the D- or L-form of alanine, glycine, proline, cysteine, histidine, glutamine, aspartic acid, isoleucine, arginine, glutamic acid, lysine, serine, phenylalanine, leucine, threonine, tryptophan, methionine, valine, tyrosine, asparagine, 2-aminoadipic acid, 2-aminoisobutyric acid, 3-aminoadipic acid, 3-aminoisobutyric acid, beta-alanine, 2-aminopimelic acid, 2-aminobutyric acid, 2,4-diaminobutyric acid, 4-aminobutyric acid, desmosine, piperidic acid, 2,2-diaminopimelic acid, 6-aminocaproic acid, 2,3-diaminopropionic acid, 2-aminoheptanoic acid, N-ethylglycine, 2-(2-thienyl)-glycine, 3-(2-thienyl)-alanine, penicillamine, sarcosine, N-ethylasparagine, N-methylisoleucine, hydroxylysine, 6-N-methyllysine, allo-hydroxylysine, N-methylvaline, 3-hydroxyproline, norvaline, 4-hydroxyproline, norleucine, isodesmosine, ornithine, allo-isoleucine, 3-(2-naphthyl)alanine, azaglycine, N-cyclohexylglycine, or 2,4-diaminobutyric acid, E is —SO$_2$—R$^4$, —CO—R$^4$;

R$^1$ is phenyl, thiazolyl, or oxazolyl, wherein the rings are unsubstituted, or are substituted up to 3 times by —(C$_1$-C$_6$)-alkyl;

R$^2$ is H, OH, CH$_2$OH, or —OMe;

R$^3$ is H, F, methyl, or —OMe;

R$^4$ is —(C$_1$-C$_{16}$-alkyl), —(C$_0$-C$_{16}$-alkylene)-R$^5$, —(C=O)—(C$_0$-C$_{16}$-alkylene)-R$^5$, —(C=O)—(C$_0$-C$_{16}$-alkylene)-NH—R$^5$, —(C$_1$-C$_8$-alkenylene)-R$^5$, —(C$_1$-C$_8$-alkynyl), —(C$_1$-C$_4$-alkylene)-S(O)$_r$—R$^5$, —(C$_1$-C$_4$-alkylene)-O—R$^5$, or —(C$_1$-C$_4$-alkylene)-NH—R$^5$;

R$^5$ is —COO—R$^6$, —(C=O)—R$^6$, —(C$_1$-C$_7$)-cycloalkyl, phenyl, naphthyl, thienyl, thiophenyl, furanyl, pyridyl, pyrimidyl, dihydropyrimidine-2,4-dion-6-yl, chromanyl, phthalimidoyl, or thiazolyl, wherein the rings are unsubstituted, or are substituted up to twice by F, Cl, Br, —OH, —CF$_3$, —NO$_2$, —CN, —OCF$_3$, —(C$_1$-C$_6$)-alkyl, —O—(C$_1$-C$_6$)-alkyl, —COOH, —COO(C$_1$-C$_6$)alkyl, —CONH$_2$, —CONH(C$_1$-C$_6$)alkyl, —CON[(C$_1$-C$_6$)alkyl]$_2$, —CONH(C$_3$-C$_6$)cycloalkyl, —NH$_2$, —NH—CO—(C$_1$-C$_6$)-alkyl, —NH—CO-phenyl, or pyridyl;

R$^6$ is H, or —(C$_1$-C$_6$)alkyl;

l, m, n are 0;

o is 1;

p is 0 or 1;

q is 0 or 1; and r is 0, 1, or 2.

4. A pharmaceutical composition, comprising at least one compound or salt thereof as claimed in claim 1 and a pharmacologically tolerated excipient.

* * * * *

UNITED STATES PATENT AND TRADEMARK OFFICE
CERTIFICATE OF CORRECTION

PATENT NO.   : 6,596,728 B1
DATED        : July 22, 2003
INVENTOR(S)  : Kirsch et al.

It is certified that error appears in the above-identified patent and that said Letters Patent is hereby corrected as shown below:

Column 75,
Line 32, "L-form" should read -- L- form --.
Line 51, "R is phenyl," should read -- $R^1$ is phenyl, --.

Column 76,
Line 50, "L-form" should read -- L- form --.

Column 77,
Line 4, "unsubtituted," should read -- unsubstituted --.

Column 78,
Line 6, "L-form," should read -- L- form --.
Line 24, after "$SO_2R^4$," and before "$CO-R^4$;", insert -- or --.

Signed and Sealed this

Twenty-third Day of September, 2003

JAMES E. ROGAN
*Director of the United States Patent and Trademark Office*